US007419671B2

(12) United States Patent
Reynolds et al.

(10) Patent No.: US 7,419,671 B2
(45) Date of Patent: Sep. 2, 2008

(54) *P. GINGIVALIS* ANTIGENIC COMPOSITION

(75) Inventors: Eric Charles Reynolds, North Balwyn (AU); Nada Slakeski, Kew (AU); Chao Guang Chen, Brunswick East (AU); Ian George Barr, Templestowe (AU)

(73) Assignees: CSL Limited, Victoria (AU); The University of Melbourne, Victoria (AU)

( * ) Notice: Subject to any disclaimer, the term of this patent is extended or adjusted under 35 U.S.C. 154(b) by 194 days.

(21) Appl. No.: 10/174,695

(22) Filed: Jun. 18, 2002

(65) Prior Publication Data

US 2003/0232022 A1 Dec. 18, 2003

Related U.S. Application Data

(63) Continuation of application No. PCT/AU00/01588, filed on Dec. 21, 2000.

(30) Foreign Application Priority Data

Dec. 24, 1999 (AU) .................................. PQ4859

(51) Int. Cl.
*A61K 39/02* (2006.01)
(52) U.S. Cl. ................. 424/190.1; 424/192.1; 530/324; 530/350
(58) Field of Classification Search .................. 424/50, 424/500
See application file for complete search history.

(56) References Cited

U.S. PATENT DOCUMENTS

| 4,603,112 A | 7/1986 | Paoletti et al. |
| 4,735,801 A | 4/1988 | Stocker |
| 4,837,151 A | 6/1989 | Stocker |
| 5,210,035 A | 5/1993 | Stocker |
| 5,824,791 A * | 10/1998 | Progulske-Fox et al. ... 536/23.7 |
| 6,511,666 B1 * | 1/2003 | Reynolds et al. ......... 424/184.1 |

FOREIGN PATENT DOCUMENTS

| WO | WO 95/07286 A1 | 3/1995 |
| WO | WO 96/17936 * | 6/1996 |
| WO | WO 97/16542 A1 | 5/1997 |
| WO | WO-97/34629 A1 | 9/1997 |

OTHER PUBLICATIONS

Sequence alingment: Acc# AAR96033.*
Sequence alingment: Acc# AAW69495.*
Sequence alingment: for patentt # 6511666.*
Rangarajan et al (Molecular Microbiology, 23(5):955-965, 1997).*
Campbell, A.M. (Monoclonal Antibody Technology, Chapter 1, pp. 1-32, Elsevier Science Publishing Company, Inc. NY, NY, 1984).*
Harlow et al (Antibodies: A Laboratory Manual, Cold Spring Harbor Press Inc., 1988, pp. 56-58, 72, 88-92 and 96-97).*
American Type Culture Collection Catalogue 1989, p. 39.*
Slakeski et al (Biocehmical and Biophysical Research Communications, 224:605-610, 1996).*
Salkeski et al (Biochemical and Biophysical Research Communications 207(1):424-431, 1995).*
Zeitlin et al (Emerging Infectious Diseases, 5:54-64, 1999).*
Dorlands Medical Dictionary, definition of gingiva.*
Stedman's Medical Dictionary, definition of gingiva.*
GenBank Accession No. AF175715, Aug. 23, 1999, located at <http://www.ncbi.nlm.nih.gov/entrez/qwuery.fcgi?cmd=Retrieve &db=nucleotide&list?> visited Aug. 27, 2002. (2 pages.).
Aduse-Opoku, J. et al. (1995). "Characterization, Genetic Analysis, and Expression of a Protease Antigen (PrpRI) of *Porphyromonas gingivalis* W50," *Infection and Immunity* 63(12):4744-4754.
Barkocy-Gallagher, G.A. et al. (1996). "Analysis of the *prtP* Gene Encoding Porphypain, a Cysteine Proteinase of *Porphyromonas gingivalis*," *Journal of Bacteriology* 178(10): 2734-2741.
Beck, J. et al. (1996). "Periodontal Disease and Cardiovascular Disease," *J. Periodontol.* 67: 1123-1137.
Beck, J.D. et al. (1998). "Periodontitis: A Risk Factor for Coronary Heart Disease?" *Annals of Periodontology* 3(1): 127-141.
Bhogal, P.S. et al. (1997). "A Cell-Associated Protein Complex of *Porphyromonas gingivalis* W50 Composed of Arg- and Lys-specific Cysteine Proteinases and Adhesins," *Microbiology* 143: 2485-2495.
Cox, J.C. and Coulter, A. R. (1992). "Advances in Adjuvant Technology and Application," Chapter 4 *In Animals Parasite Control Utilizing Technology*, Wong, W.K. ed. CRC Press: Boca Raton, FL. pp. 49-112.
Curtiss, R. III et al. (1988). "A virulent *Salmonella typhimurium* Δcya Δcrp Oral Vaccine Strains Expressing a Streptococcal Colonization and Virulence Antigen," *Vaccine.* 6: 155-160.
Dryland, A. et al. (1986). "Peptide Synthesis. Part 8. A System for Solid-Phase Synthesis Under Low Pressure Continuous Flow Conditions," *J. Chem. Soc. Perkin Trans.* I: 125-137.
Fynan, E.F. et al. (1993). "DNA Vaccines: Protective Immunizations By Parenteral, Mucosal, and Gene-Gun Inoculations," *Proc. Natl. Acad. Sci. USA*. 90: 11478-11482.
Geysen, H. M. et al. (1987). "Strategies for Epitope Analysis Using Peptide Synthesis," *Journal of Immunological Methods.* 102: 259-274.
Geysen, H. M. et al. (1984). "Use of Peptide Synthesis to Probe Viral Antigens For Epitopes to a Resolution of a Single Amino Acid," *Proc. Natl. Acad. Sci. USA*. 81: 3998-4002.
Lewis, J.P. and Macrina, F. L. (1998). "IS195, an Insertion Sequence-Like Element Associated with Protease Genes in *Porphyromonas gingivalis*," *Infection and Immunity* 66(7): 3035-3042.
Macario, A.J.L. and deMacario, E.C. eds. (1990). *Gene Probes for Bacteria*. Academic Press: New York, NY pp. vii-xii (Table of Contents).

(Continued)

*Primary Examiner*—Patricia A Duffy
(74) *Attorney, Agent, or Firm*—Morrison & Foerster LLP

(57) ABSTRACT

The present invention provides an antigenic composition, the composition comprising at least one recombinant protein. The recombinant protein comprises at least one epitope. The epitope is reactive with an antibody which is reactive with a polypeptide having the sequence set out in SEQ. ID. NO. 3 or SEQ. ID. NO. 5. The invention also provides methods and compositions for the production of the recombinant protein. Also provided are methods for the diagnosis, treatment and prevention of *P. gingivalis* infection.

12 Claims, 6 Drawing Sheets

OTHER PUBLICATIONS

Figure 1:
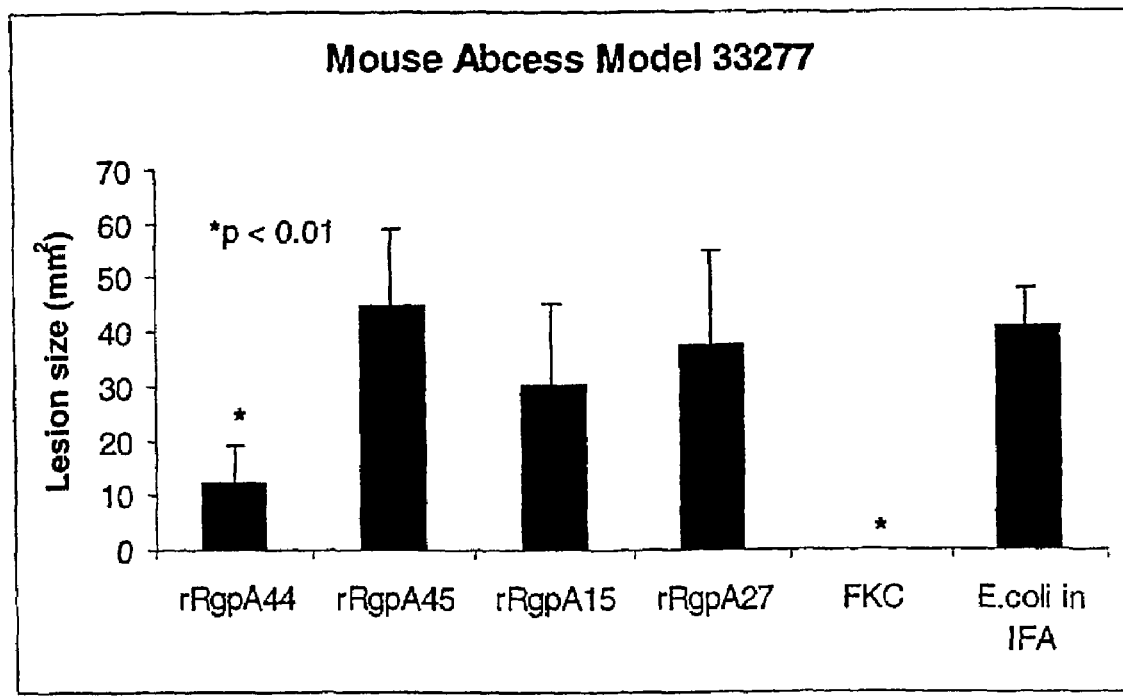

Mitchell, A.R. et al. (1978). "A New Synthetic Route to *tert*-Butyloxycarbonylaminoacyl-4-(oxymethyl) phenylacetamidomethyl-resin, an Improved Support for Solid-Phase Peptide Synthesis," *J. Org. Chem.* 43(14): 2845-2852.

Shibata, Y. et al. (1999). "Determination and Characterization of the Hemagglutinin-Associated Short Motifs Found in *Porphyromonas gingivalis* Multiple Gene Products," *The Journal of Biological Chemistry* 274(8): 5012-5020.

*Thorpe's Dictionary of Applied Chemistry*, vol. 9, 4th Edition. pp. 510-511.

Zhu, N. et al. (1993). "Systemic Gene Expression After Intravenous DNA Delivery into Adult Mice," *Science*. 261: 209-211.

Supplementary Partial European Search Report mailed on May 24, 2005, for EP Application No. 00986886.0, four pages.

American Dental Association. "Oral Health Topics A-Z:Periodontal (Gum) Disease-FAQ," located at <http://www.ada.org/public/topics/periodontal_diseases_faq.asp>last visited on Mar. 28, 2006. (3 pages).

American Dental Association. "Oral Health Topics A-Z:Periodontal (Gum) Diseases," located at <http://www.ada.org/public/topics/periodontal_diseases.asp>last visited on Mar. 28, 2006. (2 pages).

O'Brien-Simpson, N.M. et al. (2005). "An Immune Response Directed to Proteinase and Adhesin Functional Epitopes Protects against *Porphyromonas gingivalis*-Induced Periodontal Bone Loss," *Journal of Immunol.* 175(6):3980-3989.

Baker, P.J. et al. (2000). "Heterogeneity of *Porphyromonas gingivalis* Strains in the Induction of Alveolar Bone Loss in Mice," *Oral Microbiol Immunol.* 15:27-32.

Ebersole, J.L. et al. (1995). "Comparative Virulence of Periodontopathogens in a Mouse Abscess Model," *Oral Diseases* 1:115-128.

Evans, R.T. et al. (1992). "Periodontopathic Potential of Two Strains of *Porphyromonas gingivalis* in Gnotobiotic Rats," *Arch Oral Biol.* 37(10):813-819.

Griffen, A.L. et al. (Dec. 1999). "*Porphyromonas gingivalis* Strain Variability and Periodontitis," *Journal of Clinical Microbiology* 37(12):4028-4033.

Hernandez, V.G. et al. (1989). "Clinical and Clinico-Histological Markers in Chronic Destructive Adult Periodontitis," *Av Periodoncia* 1(1):33-43. [Article in Spanish]. Pub Med English Abstract located at <http://www.ncbi.nlm.nih.gov/entrez/query.fcgi?db=pubmed &cmd=Retrieve&dopt=AbstractPlus&list_uids=16148146 &query_hl=3&itool=pubmed_docsum>, last visited on Jan. 25, 2007, one page.

Kesavalu, L. et al. (1996). "Trypsin-like Protease Activity of *Porphyromonas gingivalis* as a Potential Virulence Factor in a Murine Lesion Model," *Microbial Pathogenesis* 20:1-10.

Liu, R.K. et al. (Nov. 2001). "Polymorphonuclear Neutrophils and Their Mediators in Gingival Tissues From Generalized Aggressive Periodontitis," *J. Periodontol* 72(11):1545-1553.

Marsh, P.D. et al. (1994). "The Effect of Growth Rate and Haemin on the Virulence and Proteolytic Activity of *Porphyromonas gingivalis* W50," *Microbiology* 140:861-865.

Neiders, M.E. et al. (1989). "Heterogeneity of Virulence Among Strains of *Bacteroides gingivalis*," *J. Periodont Res.* 24:192-198.

O'Brien-Simpson, N.M. et al. (2005). "An Immune Response Directed to Proteinase and Adhesin Functional Epitopes Protects Against *Porphyromonas gingivalis*-Induced Periodontal Bone Loss," *Journal of Immunology* 175(6): 3980-3989.

O'Brien-Simpson, N.M. et al. (Dec. 2001). "Role of RgpA, RgpB, and Kgp Proteinases in Virulence of *Porphyromonas gingivalis* W50 in a Murine Lesion Model," *Infection and Immunity* 69(12):7527-7534.

Schifferle, R.E. et al. (1993). "Modification of Experimental *Porphyromonas gingivalis* Murine Infection by Immunization with a Polysaccharide-Protein Conjugate," *Oral Microbiol. Immunol.* 8:266-271.

Yoneda, M. et al. (2001). "Mixed Infection of *Porphyromoas gingivalis* and *Bacteroides forsythus* in a Murine Abscess Model: Involvement of Gingipains in a Synergistic Effect," *J. Periodont. Res.* 36:237-243.

\* cited by examiner

```
                        SEQUENCE LISTING

<160> NUMBER OF SEQ ID NOS: 36

<210> SEQ ID NO 1
<211> LENGTH: 1257
<212> TYPE: DNA
<213> ORGANISM: Porphyromonas gingivalis

<400> SEQUENCE: 1
agcggtcagg ccgagattgt tcttgaagct cacgatgttt ggaatgatgg atccggttat      60
cagattcttt tggatgcaga ccatgatcaa tatggacagg ttatacccag tgatacccat     120
actctttggc cgaactgtag tgtcccggcc aatctgttcg ctccgttcga atatacggtt     180
ccggaaaatg cagatccttc ttgttcccct accaatatga taatggatgg tactgcatcc     240
gttaatatac cggccggaac ttatgacttt gcaattgctg ctcctcaagc aaatgcaaag     300
atttggattg ccggacaagg accgacgaaa gaagatgatt atgtatttga agccggtaaa     360
aaataccatt tccttatgaa gaagatgggt agcggtgatg gaactgaatt gactataagc     420
gaaggtggtg aagcgatta  cacctatact gtctatcgtg acggcacgaa gatcaaggaa     480
ggtctgacgg ctacgacatt cgaagaagac ggtgtagctg caggcaatca tgagtattgc     540
gtggaagtta agtacacagc cggcgtatct ccgaaggtat gtaaagacgt tacggtagaa     600
ggatccaatg aatttgctcc tgtacagaac ctgaccggta gtgcagtcgg ccagaaagta     660
acgcttaagt gggatgcacc taatggtacc ccgaatccaa atccaaatcc gaatccaaat     720
ccgaatcccg gaacaactac actttccgaa tcattcgaaa atggtattcc tgcctcatgg     780
aagacgatcg atgcagacgg tgacgggcat ggctggaagc ctgaaatgc  tcccggaatc     840 gctggctaca atagcaatgg ttgtgtatat tcagagtcat tcggtcttgg tggtatagga     900
```

```
gttcttaccc ctgacaacta tctgataaca ccggcattgg atttgcctaa cggaggtaag      960
ttgactttct gggtatgcgc acaggatgct aattatgcat ccgagcacta tgcggtgtat     1020
gcatcttcga ccgtaacga tgcatccaac ttcacgaatg ctttgttgga agagacgatt      1080
acggcaaaag gtgttcgctc gccggaagct attcgtggtc gtatacaggg tacttggcgc     1140
cagaagacgg tagaccttcc cgcaggtacg aaatatgttg ctttccgtca cttccaaagc     1200
acggatatgt tctacatcga ccttgatgag gttgagatca aggccaatgg caagcgc       1257
```

<210> SEQ ID NO 2
<211> LENGTH: 588
<212> TYPE: DNA
<213> ORGANISM: Porphyromonas gingivalis

<400> SEQUENCE: 2

```
aaggtatgta aagacgttac ggtagaagga tccaatgaat ttgctcctgt acagaacctg       60
accggtagtg cagtcggcca gaaagtaacg cttaagtggg atgcacctaa tggtaccccg      120
aatccaaatc caaatccgaa tccaaatccg aatcccggaa caactacact ttccgaatca      180
ttcgaaaatg gtattcctgc ctcatggaag acgatcgatc agacggtga cgggcatggc       240 tggaagcctg aaatgctcc cggaatcgct ggctacaata gcaatggttg tgtatatctc       300
gacaatagtg caaagattga tcgtaatcaa gaaatcaatg tttacaatac agctgaatat      360
gcgaagacca caacgcacc gatcaaggta gtaggttacg ctgacgaaaa aaccggtact       420
gcggcctata acatgaagct ttcagagcgt cgtgcaaaag cggtagccaa gatgcttgaa      480
aagtatggtg tttctgcgga tcgcattaca attgaatgga agggctcatc agagcaaatc      540
tatgaagaga acgcttggaa tcgtattgta gtaatgactg cagcggaa                   588
```

<210> SEQ ID NO 3
<211> LENGTH: 419
<212> TYPE: PRT
<213> ORGANISM: Porphyromonas gingivalis

<400> SEQUENCE: 3

```
Ser Gly Gln Ala Glu Ile Val Leu Glu Ala His Asp Val Trp Asn Asp
  1               5                  10                  15

Gly Ser Gly Tyr Gln Ile Leu Leu Asp Ala Asp His Asp Gln Tyr Gly
             20                  25                  30

Gln Val Ile Pro Ser Asp Thr His Thr Leu Trp Pro Asn Cys Ser Val
         35                  40                  45

Pro Ala Asn Leu Phe Ala Pro Phe Glu Tyr Thr Val Pro Glu Asn Ala
     50                  55                  60

Asp Pro Ser Cys Ser Pro Thr Asn Met Ile Met Asp Gly Thr Ala Ser
 65                  70                  75                  80

Val Asn Ile Pro Ala Gly Thr Tyr Asp Phe Ala Ile Ala Ala Pro Gln
                 85                  90                  95

Ala Asn Ala Lys Ile Trp Ile Ala Gly Gln Gly Pro Thr Lys Glu Asp
                100                 105                 110

Asp Tyr Val Phe Glu Ala Gly Lys Lys Tyr His Phe Leu Met Lys Lys
            115                 120                 125

Met Gly Ser Gly Asp Gly Thr Glu Leu Thr Ile Ser Glu Gly Gly Gly
        130                 135                 140

Ser Asp Tyr Thr Tyr Thr Val Tyr Arg Asp Gly Thr Lys Ile Lys Glu
145                 150                 155                 160
```

```
Gly Leu Thr Ala Thr Thr Phe Glu Glu Asp Gly Val Ala Ala Gly Asn
                165                 170                 175

His Glu Tyr Cys Val Glu Val Lys Tyr Thr Ala Gly Val Ser Pro Lys
            180                 185                 190

Val Cys Lys Asp Val Thr Val Glu Gly Ser Asn Glu Phe Ala Pro Val
        195                 200                 205

Gln Asn Leu Thr Gly Ser Ala Val Gly Gln Lys Val Thr Leu Lys Trp
    210                 215                 220

Asp Ala Pro Asn Gly Thr Pro Asn Pro Asn Pro Asn Pro Asn Pro Asn
225                 230                 235                 240

Pro Asn Pro Gly Thr Thr Leu Ser Glu Ser Phe Glu Asn Gly Ile
                245                 250                 255

Pro Ala Ser Trp Lys Thr Ile Asp Ala Asp Gly Asp Gly His Gly Trp
                260                 265                 270

Lys Pro Gly Asn Ala Pro Gly Ile Ala Gly Tyr Asn Ser Asn Gly Cys
            275                 280                 285

Val Tyr Ser Glu Ser Phe Gly Leu Gly Gly Ile Gly Val Leu Thr Pro
        290                 295                 300

Asp Asn Tyr Leu Ile Thr Pro Ala Leu Asp Leu Pro Asn Gly Gly Lys
305                 310                 315                 320

Leu Thr Phe Trp Val Cys Ala Gln Asp Ala Asn Tyr Ala Ser Glu His
                325                 330                 335

Tyr Ala Val Tyr Ala Ser Ser Thr Gly Asn Asp Ala Ser Asn Phe Thr
            340                 345                 350

Asn Ala Leu Leu Glu Glu Thr Ile Thr Ala Lys Gly Val Arg Ser Pro
        355                 360                 365

Glu Ala Ile Arg Gly Arg Ile Gln Gly Thr Trp Arg Gln Lys Thr Val
    370                 375                 380

Asp Leu Pro Ala Gly Thr Lys Tyr Val Ala Phe Arg His Phe Gln Ser
385                 390                 395                 400

Thr Asp Met Phe Tyr Ile Asp Leu Asp Glu Val Glu Ile Lys Ala Asn
                405                 410                 415

Gly Lys Arg

<210> SEQ ID NO 4
<211> LENGTH: 196
<212> TYPE: PRT
<213> ORGANISM: Porphyromonas gingivalis

<400> SEQUENCE: 4

Lys Val Cys Lys Asp Val Thr Val Glu Gly Ser Asn Glu Phe Ala Pro
1               5                   10                  15

Val Gln Asn Leu Thr Gly Ser Ala Val Gly Gln Lys Val Thr Leu Lys
            20                  25                  30

Trp Asp Ala Pro Asn Gly Thr Pro Asn Pro Asn Pro Asn Pro Asn Pro
        35                  40                  45

Asn Pro Asn Pro Gly Thr Thr Leu Ser Glu Ser Phe Glu Asn Gly
    50                  55                  60

Ile Pro Ala Ser Trp Lys Thr Ile Asp Ala Asp Gly Asp Gly His Gly
65                  70                  75                  80

Trp Lys Pro Gly Asn Ala Pro Gly Ile Ala Gly Tyr Asn Ser Asn Gly
                85                  90                  95

Cys Val Tyr Leu Asp Asn Ser Ala Lys Ile Asp Arg Asn Gln Glu Ile
            100                 105                 110
```

```
Asn Val Tyr Asn Thr Ala Glu Tyr Ala Lys Thr Asn Asn Ala Pro Ile
            115                 120                 125

Lys Val Val Gly Tyr Ala Asp Glu Lys Thr Gly Thr Ala Ala Tyr Asn
130                 135                 140

Met Lys Leu Ser Glu Arg Arg Ala Lys Ala Val Ala Lys Met Leu Glu
145                 150                 155                 160

Lys Tyr Gly Val Ser Ala Asp Arg Ile Thr Ile Glu Trp Lys Gly Ser
                165                 170                 175

Ser Glu Gln Ile Tyr Glu Glu Asn Ala Trp Asn Arg Ile Val Val Met
            180                 185                 190

Thr Ala Ala Glu
            195

<210> SEQ ID NO 5
<211> LENGTH: 419
<212> TYPE: PRT
<213> ORGANISM: Porphyromonas gingivalis

<400> SEQUENCE: 5

Ala Asn Glu Ala Lys Val Val Leu Ala Ala Asp Asn Val Trp Gly Asp
1               5                   10                  15

Asn Thr Gly Tyr Gln Phe Leu Leu Asp Ala Asp His Asn Thr Phe Gly
                20                  25                  30

Ser Val Ile Pro Ala Thr Gly Pro Leu Phe Thr Gly Thr Ala Ser Ser
            35                  40                  45

Asn Leu Tyr Ser Ala Asn Phe Glu Tyr Leu Ile Pro Ala Asn Ala Asp
50                  55                  60

Pro Val Val Thr Thr Gln Asn Ile Ile Val Thr Gly Gln Gly Glu Val
65                  70                  75                  80

Val Ile Pro Gly Gly Val Tyr Asp Tyr Cys Ile Thr Asn Pro Glu Pro
                85                  90                  95

Ala Ser Gly Lys Met Trp Ile Ala Gly Asp Gly Asn Gln Pro Ala
            100                 105                 110

Arg Tyr Asp Asp Phe Thr Phe Glu Ala Gly Lys Lys Tyr Thr Phe Thr
            115                 120                 125

Met Arg Arg Ala Gly Met Gly Asp Gly Thr Asp Met Glu Val Glu Asp
130                 135                 140

Asp Ser Pro Ala Ser Tyr Thr Tyr Thr Val Tyr Arg Asp Gly Thr Lys
145                 150                 155                 160

Ile Lys Glu Gly Leu Thr Ala Thr Thr Phe Glu Glu Asp Gly Val Ala
                165                 170                 175

Ala Gly Asn His Glu Tyr Cys Val Glu Val Lys Tyr Thr Ala Gly Val
            180                 185                 190

Ser Pro Lys Val Cys Lys Asp Val Thr Val Glu Gly Ser Asn Glu Phe
            195                 200                 205

Ala Pro Val Gln Asn Leu Thr Gly Ser Ser Val Gly Gln Lys Val Thr
            210                 215                 220

Leu Lys Trp Asp Ala Pro Asn Gly Thr Pro Asn Pro Asn Pro Asn Pro
225                 230                 235                 240

Asn Pro Asn Pro Gly Thr Thr Leu Ser Glu Ser Phe Glu Asn Gly Ile
                245                 250                 255

Pro Ala Ser Trp Lys Thr Ile Asp Ala Asp Gly Asp Gly His Gly Trp
            260                 265                 270

Lys Pro Gly Asn Ala Pro Gly Ile Ala Gly Tyr Asn Ser Asn Gly Cys
            275                 280                 285
```

```
Val Tyr Ser Glu Ser Phe Gly Leu Gly Gly Ile Gly Val Leu Thr Pro
    290                 295                 300

Asp Asn Tyr Leu Ile Thr Pro Ala Leu Asp Leu Pro Asn Gly Gly Lys
305                 310                 315                 320

Leu Thr Phe Trp Val Cys Ala Gln Asp Ala Asn Tyr Ala Ser Glu His
                325                 330                 335

Tyr Ala Val Tyr Ala Ser Ser Thr Gly Asn Asp Ala Ser Asn Phe Thr
                340                 345                 350

Asn Ala Leu Leu Glu Glu Thr Ile Thr Ala Lys Gly Val Arg Ser Pro
                355                 360                 365

Lys Ala Ile Arg Gly Arg Ile Gln Gly Thr Trp Arg Gln Lys Thr Val
    370                 375                 380

Asp Leu Pro Ala Gly Thr Lys Tyr Val Ala Phe Arg His Phe Gln Ser
385                 390                 395                 400

Thr Asp Met Phe Tyr Ile Asp Leu Asp Glu Val Glu Ile Lys Ala Asn
                405                 410                 415

Gly Lys Arg

<210> SEQ ID NO 6
<211> LENGTH: 231
<212> TYPE: PRT
<213> ORGANISM: Porphyromonas gingivalis

<400> SEQUENCE: 6

Phe Leu Leu Asp Ala Asp His Asn Thr Phe Gly Ser Val Ile Pro Ala
  1               5                  10                  15

Thr Gly Pro Leu Phe Thr Gly Thr Ala Ser Ser Asn Leu Tyr Ser Ala
                 20                  25                  30

Asn Phe Glu Tyr Leu Ile Pro Ala Asn Ala Asp Pro Val Val Thr Thr
             35                  40                  45

Gln Asn Ile Ile Val Thr Gly Gln Gly Glu Val Val Ile Pro Gly Gly
         50                  55                  60

Val Tyr Asp Tyr Cys Ile Thr Asn Pro Glu Pro Ala Ser Gly Lys Met
65                  70                  75                  80

Trp Ile Ala Gly Asp Gly Gly Asn Gln Pro Ala Arg Tyr Asp Asp Phe
                 85                  90                  95

Thr Phe Glu Ala Gly Lys Lys Tyr Thr Phe Thr Met Arg Arg Ala Gly
            100                 105                 110

Met Gly Asp Gly Thr Asp Met Glu Val Glu Asp Ser Pro Ala Ser
            115                 120                 125

Tyr Thr Tyr Thr Val Tyr Arg Asp Gly Thr Lys Ile Lys Glu Gly Leu
        130                 135                 140

Thr Ala Thr Thr Phe Glu Glu Asp Gly Val Ala Ala Gly Asn His Glu
145                 150                 155                 160

Tyr Cys Val Glu Val Lys Tyr Thr Ala Gly Val Ser Pro Lys Val Cys
                165                 170                 175

Lys Asp Val Thr Val Glu Gly Ser Asn Glu Phe Ala Pro Val Gln Asn
            180                 185                 190

Leu Thr Gly Ser Ser Val Gly Gln Lys Val Thr Leu Lys Trp Asp Ala
        195                 200                 205

Pro Asn Gly Thr Pro Asn Pro Asn Pro Asn Pro Asn Pro Asn Pro Gly
    210                 215                 220

Thr Thr Leu Ser Glu Ser Phe
225                 230
```

<210> SEQ ID NO 7
<211> LENGTH: 1257
<212> TYPE: DNA
<213> ORGANISM: Porphyromonas gingivalis

<400> SEQUENCE: 7

| | | | | | |
|---|---|---|---|---|---|
| gccaacgaag | ccaaggttgt | gcttgcggca | gacaacgtat | ggggagacaa | tacgggttac | 60 |
| cagttcttgt | tggatgccga | tcacaataca | ttcggaagtg | tcattccggc | aaccggtcct | 120 |
| ctctttaccg | gaacagcttc | ttccaatctt | tacagtgcga | acttcgagta | tttgatcccg | 180 |
| gccaatgccg | atcctgttgt | tactacacag | aatattatcg | ttacaggaca | gggtgaagtt | 240 |
| gtaatccccg | tggtgttta | cgactattgc | attacgaacc | cggaacctgc | atccggaaag | 300 |
| atgtggatcg | caggagatgg | aggcaaccag | cctgcacgtt | atgacgattt | cacattcgaa | 360 |
| gcaggcaaga | agtacacctt | cacgatgcgt | cgcgccggaa | tggagatgg | aactgatatg | 420 |
| gaagtcgaag | acgattcacc | tgcaagctat | acctacacgg | tgtatcgtga | cggcacgaag | 480 |
| atcaaggaag | gtctgacagc | tacgacattc | gaagaagacg | gtgtagctgc | aggcaatcat | 540 |
| gagtattgcg | tggaagttaa | gtacacagcc | ggcgtatctc | cgaaggtatg | taaagacgtt | 600 |
| acggtagaag | gatccaatga | atttgctcct | gtacagaacc | tgaccggtag | ttcagtaggt | 660 |
| cagaaagtaa | cgcttaagtg | ggatgcacct | aatggtaccc | cgaatccgaa | tccaaatccg | 720 |
| aatccgaatc | cgggaacaac | actttccgaa | tcattcgaaa | atggtattcc | ggcatcttgg | 780 |
| aagacgatcg | atgcagacgg | tgacgggcat | ggctggaaac | ctggaaatgc | tcccggaatc | 840 |
| gctggctaca | atagcaatgg | ttgtgtatat | tcagagtcat | tcggtcttgg | tggtatagga | 900 |
| gttcttaccc | ctgacaacta | tctgataaca | ccggcattgg | atttgcctaa | cggaggtaag | 960 |
| ttgactttct | gggtatgcgc | acaggatgct | aattatgcat | ccgagcacta | tgcggtgtat | 1020 |
| gcatcttcga | ccgtaacga | tgcatccaac | ttcacgaatg | ctttgttgga | agagacgatt | 1080 |
| acggcaaaag | gtgttcgctc | gccgaaagct | attcgtggtc | gtatacaggg | tacttggcgc | 1140 |
| cagaagacg | tagaccttcc | cgcaggtacg | aaatatgttg | ctttccgtca | cttccaaagc | 1200 |
| acggatatgt | tctacatcga | ccttgatgag | gttgagatca | aggccaatgg | caagcgc | 1257 |

<210> SEQ ID NO 8
<211> LENGTH: 693
<212> TYPE: DNA
<213> ORGANISM: Porphyromonas gingivalis

<400> SEQUENCE: 8

| | | | | | |
|---|---|---|---|---|---|
| ttcttgttgg | atgccgatca | caatacattc | ggaagtgtca | ttccggcaac | cggtcctctc | 60 |
| tttaccggaa | cagcttcttc | caatctttac | agtgcgaact | tcgagtattt | gatcccggcc | 120 |
| aatgccgatc | ctgttgttac | tacacagaat | attatcgtta | caggacaggg | tgaagttgta | 180 |
| atccccggtg | tgtttacga | ctattgcatt | acgaacccgg | aacctgcatc | cggaaagatg | 240 |
| tggatcgcag | gagatggagg | caaccagcct | gcacgttatg | acgatttcac | attcgaagca | 300 |
| ggcaagaagt | acaccttcac | gatgcgtcgc | gccggaatgg | agatggaac | tgatatggaa | 360 |
| gtcgaagacg | attcacctgc | aagctatacc | tacacggtgt | atcgtgacgg | cacgaagatc | 420 |
| aaggaaggtc | tgacagctac | gacattcgaa | gaagacggtg | tagctgcagg | caatcatgag | 480 |
| tattgcgtgg | aagttaagta | cacagccggc | gtatctccga | aggtatgtaa | agacgttacg | 540 |
| gtagaaggat | ccaatgaatt | tgctcctgta | cagaacctga | ccggtagttc | agtaggtcag | 600 |

```
aaagtaacgc ttaagtggga tgcacctaat ggtaccccga atccgaatcc aaatccgaat    660
ccgaatccgg gaacaacact ttccgaatca ttc                                  693
```

<210> SEQ ID NO 9
<211> LENGTH: 26
<212> TYPE: DNA
<213> ORGANISM: Porphyromonas gingivalis

<400> SEQUENCE: 9

```
gcgcagatct tacacaccgg tagagg                                           26
```

<210> SEQ ID NO 10
<211> LENGTH: 29
<212> TYPE: DNA
<213> ORGANISM: Porphyromonas gingivalis

<400> SEQUENCE: 10

```
gcgcgtcgac ttagcgaaga agttcgggg                                        29
```

<210> SEQ ID NO 11
<211> LENGTH: 35
<212> TYPE: DNA
<213> ORGANISM: Porphyromonas gingivalis

<400> SEQUENCE: 11

```
gcgccatatg agcggtcagg ccgagattgt tcttg                                 35
```

<210> SEQ ID NO 12
<211> LENGTH: 34
<212> TYPE: DNA
<213> ORGANISM: Porphyromonas gingivalis

<400> SEQUENCE: 12

```
gcgcctcgag gcgcttgcca ttggccttga tctc                                  34
```

<210> SEQ ID NO 13
<211> LENGTH: 35
<212> TYPE: DNA
<213> ORGANISM: Porphyromonas gingivalis

<400> SEQUENCE: 13

```
gcgcgctagc gtatacatgg ccaacgaagc caagg                                 35
```

<210> SEQ ID NO 14
<211> LENGTH: 28
<212> TYPE: DNA
<213> ORGANISM: Porphyromonas gingivalis

<400> SEQUENCE: 14

```
gcgcagatct cttgatagcg agtttctc                                         28
```

<210> SEQ ID NO 15
<211> LENGTH: 40
<212> TYPE: DNA
<213> ORGANISM: Porphyromonas gingivalis

<400> SEQUENCE: 15

```
gcgcgctagc gtatacatgg cagacttcac ggaaacgttc                            40
```

<210> SEQ ID NO 16
<211> LENGTH: 30
<212> TYPE: DNA
<213> ORGANISM: Porphyromonas gingivalis

```
<400> SEQUENCE: 16
gcgcagatct tttggcgcca tcggcttccg                                    30

<210> SEQ ID NO 17
<211> LENGTH: 30
<212> TYPE: DNA
<213> ORGANISM: Porphyromonas gingivalis

<400> SEQUENCE: 17
gggaattcca tgggtcaggc cgagattgtt                                    30

<210> SEQ ID NO 18
<211> LENGTH: 30
<212> TYPE: DNA
<213> ORGANISM: Porphyromonas gingivalis

<400> SEQUENCE: 18
tccctcgagc ttaacttcca cgcaatactc                                    30

<210> SEQ ID NO 19
<211> LENGTH: 30
<212> TYPE: DNA
<213> ORGANISM: Porphyromonas gingivalis

<400> SEQUENCE: 19
gggaattcca tgggtcaggc cgagattgtt                                    30

<210> SEQ ID NO 20
<211> LENGTH: 35
<212> TYPE: DNA
<213> ORGANISM: Porphyromonas gingivalis

<400> SEQUENCE: 20
ggtcaattgg actcgagata tacacaacca ttgct                              35

<210> SEQ ID NO 21
<211> LENGTH: 30
<212> TYPE: DNA
<213> ORGANISM: Porphyromonas gingivalis

<400> SEQUENCE: 21
gaggaattca gatccttctt gttcccctac                                    30

<210> SEQ ID NO 22
<211> LENGTH: 30
<212> TYPE: DNA
<213> ORGANISM: Porphyromonas gingivalis

<400> SEQUENCE: 22
tccctcgagc ttaacttcca cgcaatactc                                    30

<210> SEQ ID NO 23
<211> LENGTH: 30
<212> TYPE: DNA
<213> ORGANISM: Porphyromonas gingivalis

<400> SEQUENCE: 23
gaggaattca gatccttctt gttcccctac                                    30

<210> SEQ ID NO 24
<211> LENGTH: 35
<212> TYPE: DNA
```

```
<213> ORGANISM: Porphyromonas gingivalis

<400> SEQUENCE: 24
ggtcaattgg actcgagata tacacaacca ttgct                              35

<210> SEQ ID NO 25
<211> LENGTH: 30
<212> TYPE: DNA
<213> ORGANISM: Porphyromonas gingivalis

<400> SEQUENCE: 25
gaggaattca gatccttctt gttcccctac                                    30

<210> SEQ ID NO 26
<211> LENGTH: 31
<212> TYPE: DNA
<213> ORGANISM: Porphyromonas gingivalis

<400> SEQUENCE: 26
aggaattctc gagcttgccg ttggccttga t                                  31

<210> SEQ ID NO 27
<211> LENGTH: 33
<212> TYPE: DNA
<213> ORGANISM: Porphyromonas gingivalis

<400> SEQUENCE: 27
gggaattcca tggcgaaggt atgtaaagac gtt                                33

<210> SEQ ID NO 28
<211> LENGTH: 35
<212> TYPE: DNA
<213> ORGANISM: Porphyromonas gingivalis

<400> SEQUENCE: 28
ggtcaattgg actcgagata tacacaacca ttgct                              35

<210> SEQ ID NO 29
<211> LENGTH: 33
<212> TYPE: DNA
<213> ORGANISM: Porphyromonas gingivalis

<400> SEQUENCE: 29
gggaattcca tggcgaaggt atgtaaagac gtt                                33

<210> SEQ ID NO 30
<211> LENGTH: 31
<212> TYPE: DNA
<213> ORGANISM: Porphyromonas gingivalis

<400> SEQUENCE: 30
aggaattctc gagcttgccg ttggccttga t                                  31

<210> SEQ ID NO 31
<211> LENGTH: 32
<212> TYPE: DNA
<213> ORGANISM: Porphyromonas gingivalis

<400> SEQUENCE: 31
ggcccatggt cgacaatagt gcaaagattg at                                 32

<210> SEQ ID NO 32
<211> LENGTH: 35
```

```
-continued

<212> TYPE: DNA
<213> ORGANISM: Porphyromonas gingivalis

<400> SEQUENCE: 32
ctatccggcc gcttccgctg cagtcattac tacaa                          35

<210> SEQ ID NO 33
<211> LENGTH: 31
<212> TYPE: DNA
<213> ORGANISM: Porphyromonas gingivalis

<400> SEQUENCE: 33
gcagcagtcg acgccaacga agccaaggtt g                              31

<210> SEQ ID NO 34
<211> LENGTH: 28
<212> TYPE: DNA
<213> ORGANISM: Porphyromonas gingivalis

<400> SEQUENCE: 34
gcagcactcg aggcgcttgc cattggcc                                  28

<210> SEQ ID NO 35
<211> LENGTH: 33
<212> TYPE: DNA
<213> ORGANISM: Porphyromonas gingivalis

<400> SEQUENCE: 35
gcagcagtcg acttcttgtt ggatgccgat cac                            33

<210> SEQ ID NO 36
<211> LENGTH: 32
<212> TYPE: DNA
<213> ORGANISM: Porphyromonas gingivalis

<400> SEQUENCE: 36
gcagcactcg aggaatgatt cggaaagtgt tg                             32
```

P. GINGIVALIS ANTIGENIC COMPOSITION

CROSS REFERENCE TO RELATED APPLICATIONS

This application is a continuation of international Application No. PCT/AU00/01588, filed Dec. 21, 2000, and published in English on Jul. 5, 2001, which claims the benefit of Australian Application No. PQ 4859, filed Dec. 24, 1999, the contents of each are incorporated herein by reference.

FIELD OF THE INVENTION

This invention provides an oral composition and an antigenic composition for use in the suppression of the pathogenic effects of the intra-oral bacterium *Porphyromonas gingivalis* associated with periodontal disease based on recombinant protein and antibodies. It also provides diagnostic tests for the presence of *P. gingivalis* in subgingival plaque samples and specific anti-*P. gingivalis* antibodies in sera. Related thereto and disclosed is a method for preparing r-RgpA44 and r-Kgp39 and derivatives thereof using recombinant DNA techniques. Also disclosed are host cells transformed with recombinant vectors capable of expressing the recombinant proteins. The recombinant proteins are useful as immunogens in a vaccine formulation for active immunization and can be used to generate protein-specific antisera useful for passive immunization and as reagents for diagnostic assays.

BACKGROUND OF THE INVENTION

This invention relates generally to recombinant proteins of *Porphyromonas gingivalis*, r-RgpA44 and r-Kgp39. The invention also relates to pharmaceutical compositions and associated agents based on these recombinant proteins and derivatives for the detection, prevention and treatment of periodontal disease associated with *P. gingivalis*.

Periodontal diseases are bacterial-associated inflammatory diseases of the supporting tissues of the teeth and range from the relatively mild form of gingivitis, the non-specific, reversible inflammation of gingival tissue to the more aggressive forms of periodontitis which are characterised by the destruction of the tooth's supporting structures. Periodontitis is associated with a subgingival infection of a consortium of specific Gram-negative bacteria that leads to the destruction of the periodontium and is a major public health problem. One bacterium that has attracted considerable interest is *P. gingivalis* as the recovery of this microorganism from adult periodontitis lesions can be up to 50% of the subgingival anaerobically cultivable flora, whereas *P. gingivalis* is rarely recovered, and then in low numbers, from healthy sites. A proportional increase in the level of *P. gingivalis* in subgingival plaque has been associated with an increased severity of periodontitis and eradication of the microorganism from the cultivable subgingival microbial population is accompanied by resolution of the disease. The progression of periodontitis lesions in non-human primates has been demonstrated with the subgingival implantation of *P. gingivalis*. These findings in both animals and humans suggest a major role for *P. gingivalis* in the development of adult periodontitis.

More recently there has been increasing linkage of periodontal disease and cardiovascular disease and therefore a link between *P. gingivalis* infection and cardiovascular disease. More information regarding this linkage can be found in Beck, J D et al. Ann Periodontol. 3: 127-141, 1998 and Beck, J. et al. J. Periodontol. 67:1123-37, 1996.

*P. gingivalis* expresses a range of proteins on its cell surface that are potential candidates for the development of a vaccine or diagnostic. A major group of cell surface proteins expressed by *P. gingivalis* is a group of proteinases and associated adhesins. One proteinase designated Arg-gingipain has been disclosed previously by Travis et al. (PCT Publication No. WO 95/07286). These investigators also reported a high molecular mass form of Arg-gingipain that is encoded by the gene rgp also disclosed in WO 95/07286. The high molecular mass form of Arg-gingipain consists of the proteinase and several other proteins proposed to be adhesins. Cell-surface complexes of *P. gingivalis* consisting of Arg- and Lys-specific proteinases and adhesins have also been disclosed by Reynolds et al. (PCT/AU96/00673). Neither of these disclosures provide teaching regarding the utility of a particular adhesin as a recombinant in the protection of *P. gingivalis* infection.

SUMMARY OF THE INVENTION

In a first aspect the present invention consists in an antigenic composition, the composition comprising at least one recombinant protein having a molecular weight of less than or equal to 44 kDa as estimated by SDS-PAGE, wherein the recombinant protein comprises at least one epitope, the epitope being reactive with an antibody wherein the antibody is reactive with a polypeptide having the sequence set out in SEQ. ID. NO. 3 or SEQ. ID. NO. 5.

In a further preferred embodiment the antigenic composition comprises a recombinant protein having a sequence selected from the group consisting of SEQ. ID. NO. 3, residues 1-184 of SEQ. ID. NO. 3, residues 1-290 of SEQ. ID. NO. 3, residues 65-184 of SEQ. ID. NO. 3, residues 65-290 of SEQ. ID. NO. 3, residues 65-419 of SEQ. ID. NO. 3, residues 192-290 of SEQ. ID. NO. 3, residues 192-419 of SEQ. ID. NO. 3, residues 147-419 of SEQ. ID. NO. 3, SEQ. ID. NO. 5 and SEQ. ID. NO. 6.

As will be noted from a comparison of SEQ. ID. NO. 3 and SEQ. ID. NO. 5 these polypeptides are identical over a substantial portion of their sequence.

In another preferred embodiment the antigenic composition further comprises an adjuvant.

In yet another preferred embodiment the recombinant protein is a chimeric or a fusion protein. Where the recombinant protein is a chimeric or a fusion protein it is preferred that protein include a sequence selected from the group consisting of SEQ. ID. NO. 3, residues 1-184 of SEQ. ID. NO. 3, residues 1-290 of SEQ. ID. NO. 3, residues 65-184 of SEQ. ID. NO. 3, residues 65-290 of SEQ. ID. NO. 3, residues 65-419 of SEQ. ID. NO. 3, residues 192-290 of SEQ. ID. NO. 3, residues 192-419 of SEQ. ID. NO. 3, residues 147-419 of SEQ. ID. NO. 3, SEQ. ID. NO. 5 and SEQ. ID. NO. 6. An example of such a chimeric or a fusion protein is set out in SEQ. ID. NO. 4.

In a second aspect the present invention consists in a composition, the composition comprising at least one antibody, the antibody being raised against the antigenic composition of the first aspect of the present invention.

In a third aspect the present invention consists in a recombinant prokaryotic or eucaryotic cell, the recombinant cell comprising an introduced DNA sequence selected from the group consisting of SEQ. ID. NO. 1, nucleotides 1-1257 of SEQ. ID. NO. 1, nucleotides 1-552 of SEQ. ID. NO. 1, nucleotides 1-870 of SEQ. ID. NO. 1, nucleotides 193-552 of SEQ. ID. NO. 1, nucleotides 193-870 of SEQ. ID. NO. 1, nucleotides 193-1257 of SEQ. ID. NO. 1, nucleotides 574-870 of SEQ. ID. NO. 1, nucleotides 574-1257 of SEQ. ID. NO. 1, nucleotides 439-1257 of SEQ. ID. NO. 1, SEQ. ID NO. 7, SEQ. ID. NO. 8 and sequences which hybridise thereto under stringent conditions operatively linked to at least one regulatory element, such that said recombinant cell is capable of expressing a recombinant protein having a molecular weight of less than or equal to 44 kDa as estimated by SDS-PAGE, wherein the recombinant protein comprises at least one epitope, the epitope being reactive with an antibody wherein the antibody is reactive with a polypeptide having the sequence set out in SEQ ID NO: 3 or SEQ ID NO: 5.

As used herein, stringent conditions are those that (1) employ low ionic strength and high temperature for washing, for example, 0.015 M NaCl/0.0015 M sodium citrate/0.1% NaDodSO$_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 g/ml), 0.1% SDS and 10% dextran sulfate at 42° C. in 0.2×SSC and 0.1% SDS.

In a further aspect the present invention consists in a method of preventing or reducing the incidence or severity of *P. gingivalis* infection in a subject, the method comprising administering to the subject the antigenic composition of the first aspect of the present invention.

Given the increasing linkage of periodontal disease with cardiovascular disease (CVD) and the possible link therefore of *P. gingivalis* infection and CVD the antigenic composition of the first aspect of the present invention may also be used in a prophylactic therapy to reduce the incidence or severity of CVD or as an adjunct in treating CVD.

An important form of the invention is a vaccine based on the r-RgpA44 and/or r-Kgp39 proteins or peptides and suitable adjuvant delivered by nasal spray, orally or by injection to produce a specific immune response against the RgpA44 and/or r-Kgp39 protein. A vaccine can also be based upon a recombinant component of the RgpA44 and/or Kgp39 gene segment incorporated into an appropriate vector and expressed in a suitable transformed host (e.g. *E. coli, Bacillus subtilis, Saccharomyces cerevisiae*, COS cells, CHO cells and HeLa cells) containing the vector. Component protein, peptides, and oligopeptides with immunogenic epitopes from the RgpA44 and/or Kgp39 protein, can be used as immunogens in various vaccine formulations in the prevention of periodontal diseases. Additionally, according to the present invention, the RgpA44 and/or Kgp39 proteins and related peptides or chimeras produced may be used to generate *P. gingivalis* antisera useful for passive immunization against periodontal disease and infections caused by *P. gingivalis*.

According to one embodiment of the present invention, using recombinant DNA techniques the gene segment encoding RgpA44 and/or Kgp39, or gene fragments encoding one or more peptides or chimeras having immunogenic epitopes, is incorporated into an expression vector, and the recombinant vector is introduced into an appropriate host cell thereby directing the expression of these sequences in that particular host cell. The expression system, comprising the recombinant vector introduced into the host cell, can be used (a) to produce r-RgpA44 and/or r-Kgp39 proteins, related peptides, oligopeptides or chimeras which can be purified for use as an immunogen in vaccine formulations; (b) to produce RgpA44 and/or Kgp39 protein, related peptides, oligopeptides and chimeras to be used as an antigen for diagnostic immunoassays or for generating *P. gingivalis*-specific antisera of therapeutic and/or diagnostic value; (c) or if the recombinant expression vector is a live virus such as vaccinia virus, the vector itself may be used as a live or inactivated vaccine preparation to be introduced into the host's cells for expression of RgpA44 and/or Kgp39 or immunogenic peptides or oligopeptides or chimeric peptides; (d) for introduction into live attenuated bacterial cells or genetically engineered commensal intra-oral bacteria which are used to express RgpA44 and/or Kgp39 protein, related peptides or oligopeptides or chimeras to vaccinate individuals; (e) or for introduction directly into an individual to immunize against the encoded and expressed RgpA44 protein, related peptides, or oligopeptides or chimeras. In particular the recombinant bacterial vaccine can be based on a commensal inhabitant of the human oral cavity or animal if the vaccine is to prevent periodontal disease in animals. The recombinant bacterial vaccine expressing *P. gingivalis* RgpA44 and/or Kgp39 can be used to colonise the oral cavity, supragingival or subgingival plaque. The intra-oral bacterium can be isolated from the patient with periodontitis and genetically engineered to express the r-RgpA44 and/or r-Kgp39, components, peptides or chimeras. The r-RgpA44 and/or r-Kgp39 protein will stimulate the mucosal-associated lymphoid tissues (NIALT) to produce specific antibody to *P. gingivalis*.

RgpA44 and/or Kgp39 proteins, peptides, oligopeptides, chimeric peptides and constructs containing epitopes can be used as immunogens in prophylactic and/or therapeutic vaccine formulations against pathogenic strains of *P. gingivalis*, whether the immunogen is chemically synthesized, purified from *P. gingivalis*, or purified from a recombinant expression vector system. Alternatively, the gene segment encoding RgpA44 and/or Kgp39, or one or more gene fragments encoding peptides or oligopeptides or chimeric peptides, may be incorporated into a bacterial or viral vaccine comprising recombinant bacteria or virus which is engineered to produce one or more specific immunogenic epitopes of RgpA44 and/or Kgp39, or in combination with immunogenic epitopes of other pathogenic microorganisms. In addition, the gene encoding RgpA44 and/or Kgp39 or one or more gene fragments encoding RgpA44 and/or Kgp39 peptides or oligopeptides or chimeric peptides, operatively linked to one or more regulatory elements, can be introduced directly into humans to express protein, peptide, oligopeptides or chimeric peptides relating to the RgpA44 and/or Kgp39 to elicit a protective immune response. A vaccine can also be based upon a recombinant component of normal or mutated RgpA44 and/or Kgp39 incorporated into an appropriate vector and expressed in a suitable transformed host (e.g. *E. coli, Bacillus subtilis, Saccharomyces cerevisiae*, COS cells, CHO cells and HeLa cells) containing the vector. The vaccine can be based on an intra-oral recombinant bacterial vaccine, where the recombinant bacterium expressing the *P. gingivalis* RgpA44 and/or Kgp39 is a commensal inhabitant of the oral cavity.

In another aspect, the invention provides nucleotide sequences coding for the recombinant protein and functional equivalents of said nucleotide sequences and nucleic acid probes for said nucleotide sequences.

The invention also includes within its scope various applications and uses of the above nucleotides and recombinant products including chimeric recombinant polypeptides. In particular, the invention provides antibodies raised against the r-RgpA44 or r-Kgp39, herein called anti-r-RgpA44 antibodies and anti-r-Kgp39 antibodies, respectively; and antibodies to the polypeptides, oligopeptides and chimeric peptides. The antibodies may be polyclonal or monoclonal. The antibodies may be blended into oral compositions such as toothpaste, mouthwash, toothpowders and liquid dentifrices, mouthwashes, troches, chewing gums, dental pastes, gingival massage creams, gargle tablets, dairy products and other foodstuffs. The recombinant polypeptides, oligopeptides and chimeric peptides may also be used as immunogens in prophylactic and/or therapeutic vaccine formulations.

In another aspect the invention provides a method of diagnosis for the presence of *P. gingivalis* characterised by the use of any one or a combination of an antibody, antigen or nucleic acid probe as hereinbefore defined comprising the application of known techniques including for example, enzyme linked immunosorbent assay.

The invention also provides diagnostic kits comprising antibodies, antigens and/or nucleic acid probes as hereinbefore defined.

The invention also provides a method of treatment of a patient either suffering from *P. gingivalis* infection comprising active vaccination of said patient with a vaccine as hereinbefore defined and/or passive vaccination of said patient with an antibody as hereinbefore defined.

DETAILED DESCRIPTION OF THE INVENTION

Figure Legends

FIG. 1 shows the results obtained in Example 1.

Figure 2:
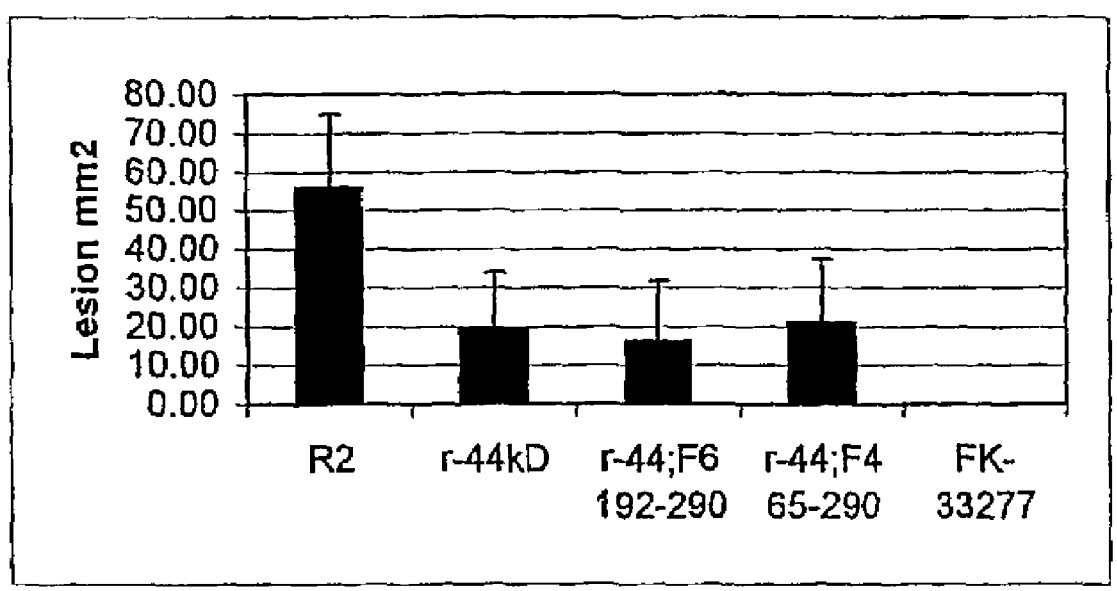

FIG. 2 shows the results of the full length recombinant 44 kD protein, 2 fragments of the 44 kD protein (Fragment 4; residues 65-290 and fragment 6; residues 192-290), a control recombinant protein R2 and Formalin killed whole *P. gingivalis* (FK-33277) in the mouse abscess model.

Figure 3:
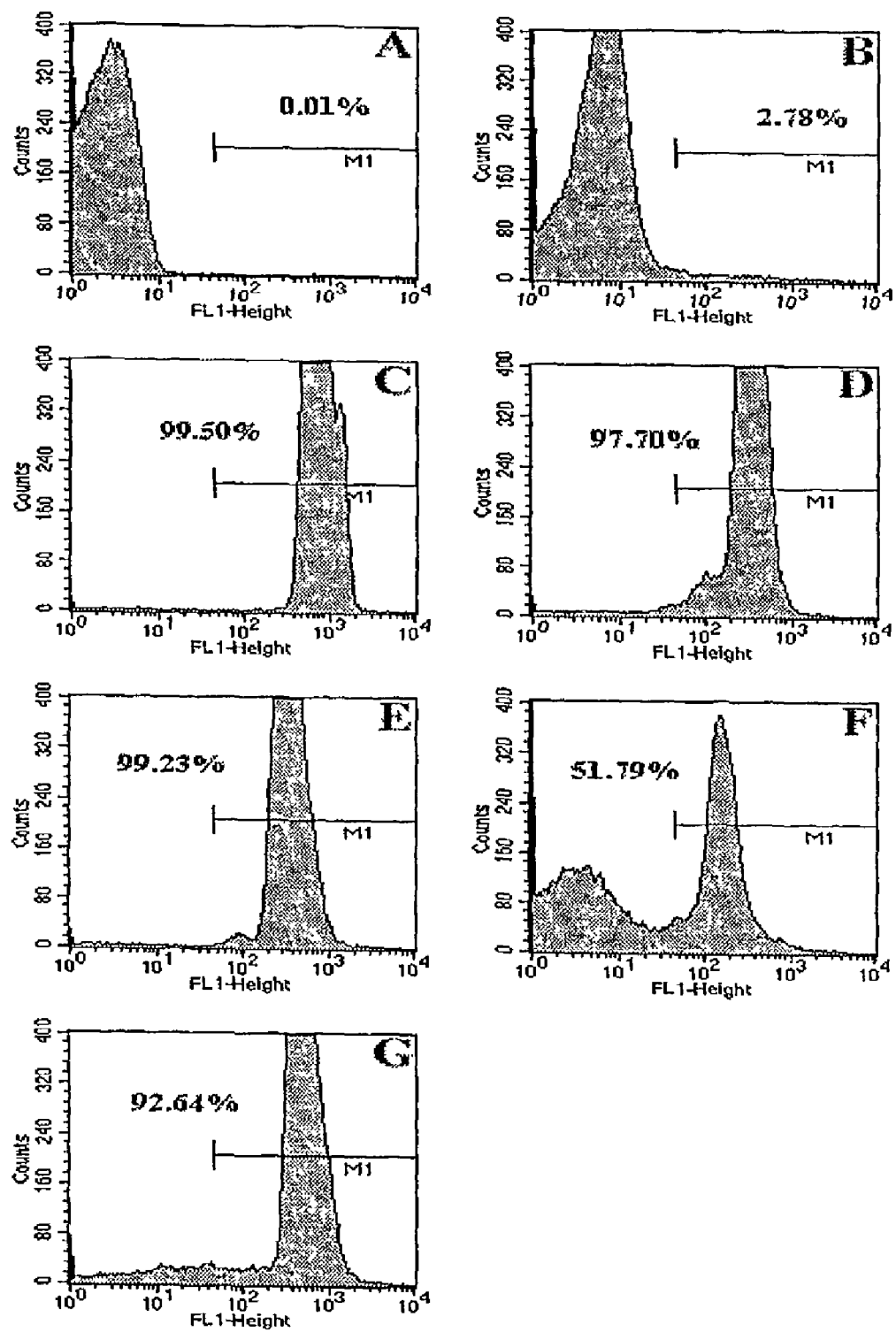

FIG. 3. Flow cytometric analysis of *P. gingivalis* cells reacted with (A) PBS/FA, (B) normal mouse serum, (C) *P. gingivalis* whole cell antisera, (D) recombinant Pg44 antisera, (E) Fragment 4 antisera (r-44 kDa residues 65-290) (F) Fragment 6 antisera (r-44 kDa residues 192-290) (G) Chimeric r-44-Pg33 protein antisera.

Figure 4:
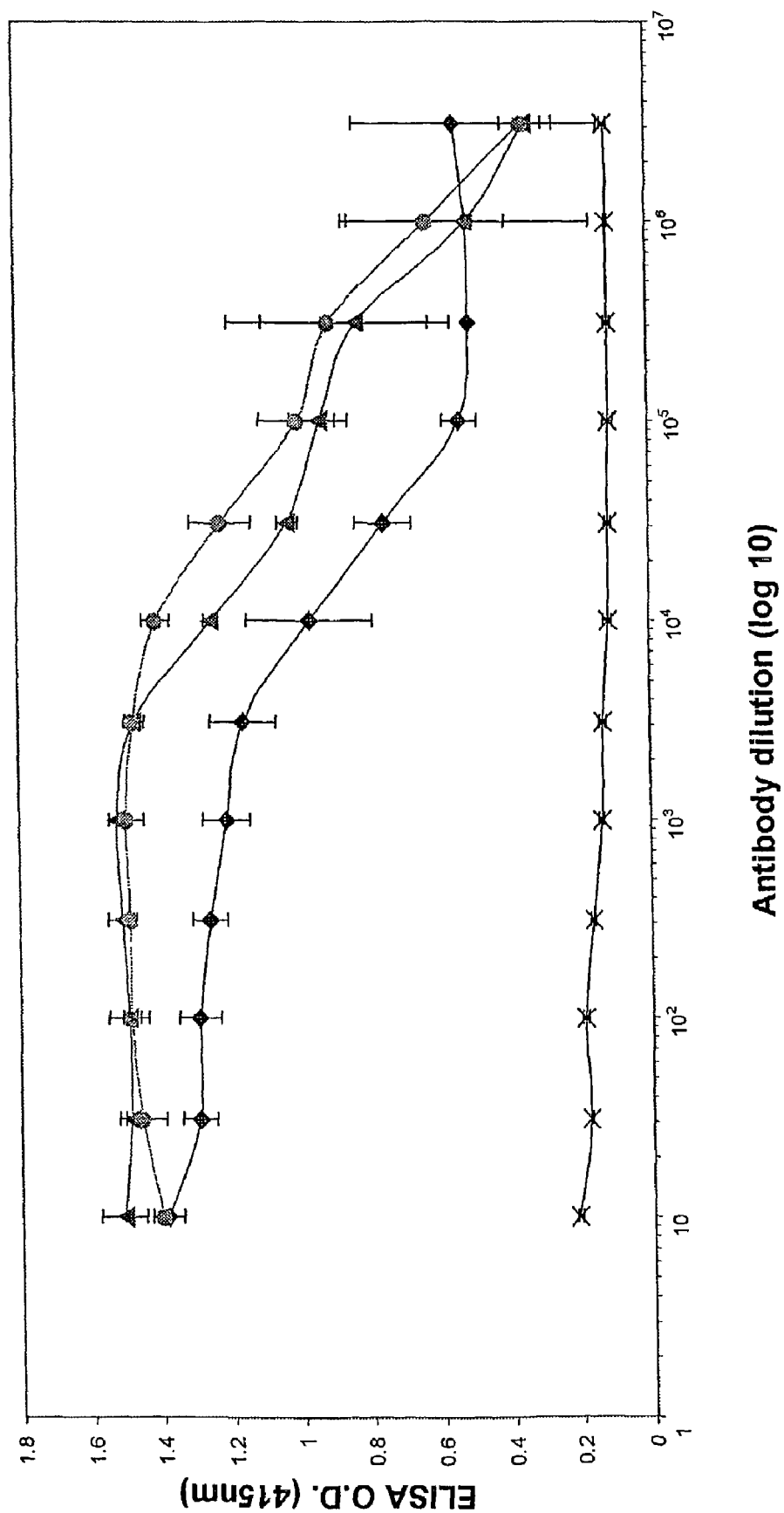

FIG. 4. Binding of the RgpA-Kgp specific anti-sera to recombinant proteins. The recombinant proteins were coated at 5 µg/ml and probed with anti-RgpA-Kgp specific anti-sera: recombinant Kgp39 protein (-♦-), recombinant Kgp39 fragment (-▲-), RgpA-Kgp complex (-●-), and control (-X-). Bound antibody was detected using a 1:4000 dilution of Goat anti-Rabbit HRP, and ELISA plates were read using a Labsystems iEMS microplate reader at 415 nm.

Figure 5:
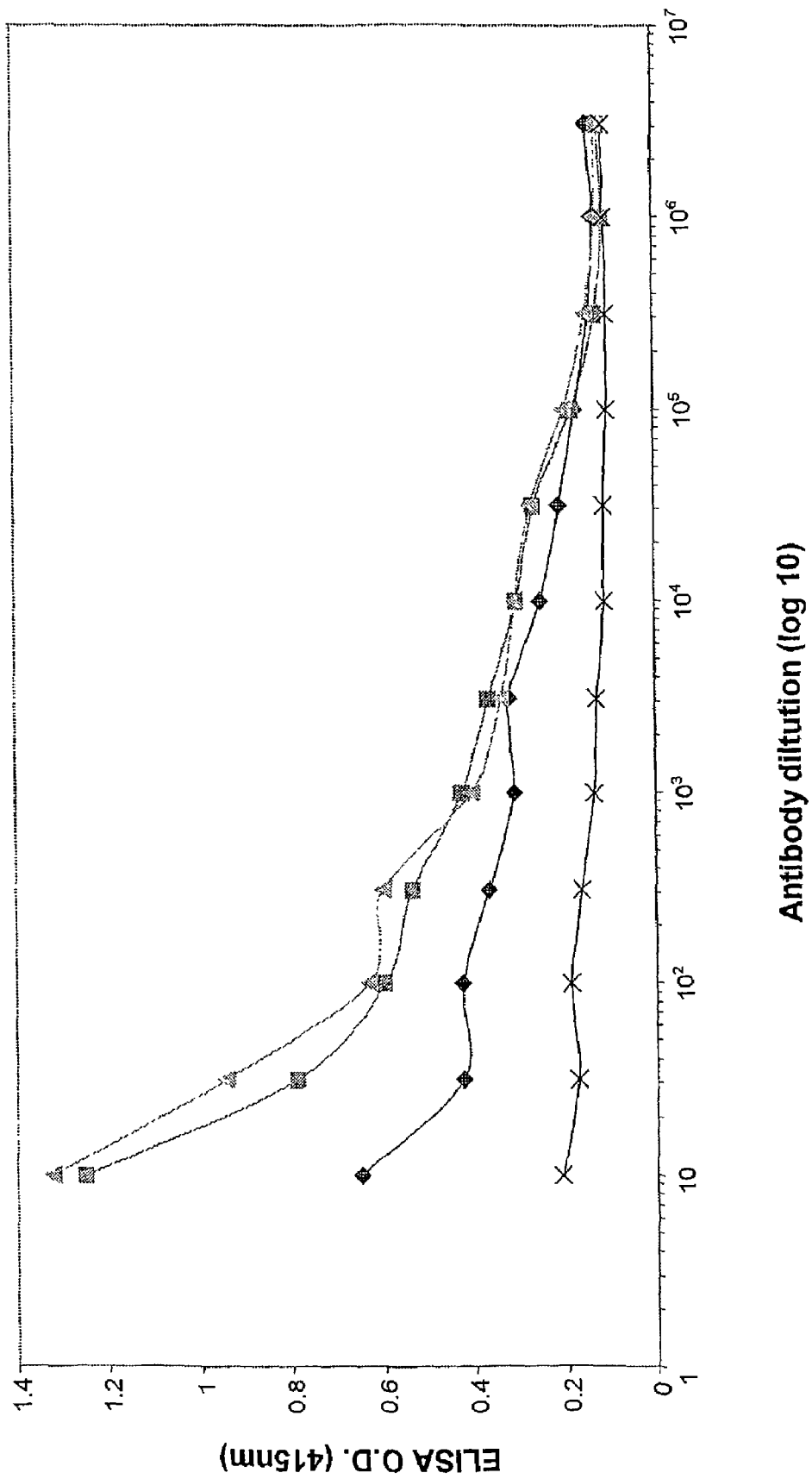

FIG. 5. Binding of recombinant Kgp39 protein to a variety of matrix proteins. The matrix proteins were coated at 5 µg/ml and probed with recombinant protein which was then probed with anti-RgpA-Kgp complex specific anti-sera: Collagen type V (-♦-), Fibrinogen (-■-), Hemoglobin (-▲-), and control (-X-). Bound antibody was detected using a 1:4000 dilution of Goat anti-Rabbit HRP conjugate, and ELISA plates were read using a Labsystems iEMS reader at 415 nm.

Figure 6:
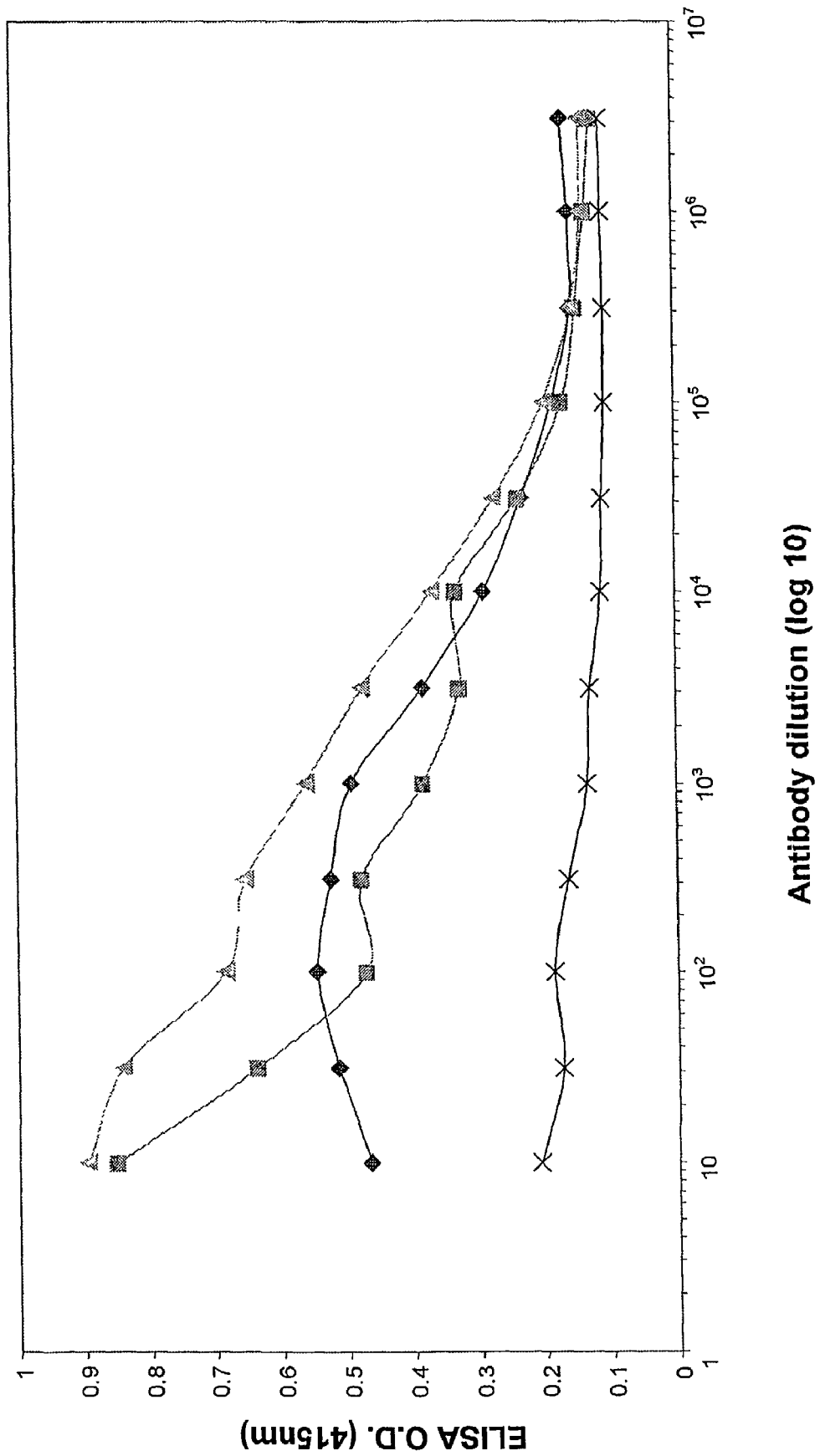

FIG. 6. Binding of recombinant Kgp39 protein fragment to a variety of matrix proteins. The matrix proteins were coated at 5 µg/ml and probed with recombinant protein which was then probed with anti-RgpA-Kgp complex specific anti-sera: Collagen type V (-♦-), Fibrinogen (-■-), Hemoglobin (-▲-), and control (-X-). Bound antibody was detected using a 1:4000 dilution of Goat anti-Rabbit HRP conjugate, and ELISA plates were read using a Labsystems IEMS reader at 415 nm.

In order that the nature of the present invention may be more clearly understood preferred forms thereof will be described with reference to the following Examples.

The intra-oral bacterium *Porphyromonas gingivalis* contains on its surface a proteinase-adhesin complex encoded by the genes rgpA and kgp. The recombinant 44 kDa adhesin (r-RgpA44) of this proteinase-adhesin complex protects against *P. gingivalis* challenge in a mouse abscess model whereas other recombinant proteins from the rgpA gene do not. The gene segment encoding the 44 kDa adhesin domain RgpA44 or Kgp39 can be cloned into an appropriate expression system to produce the recombinant protein, r-RgpA44 or r-Kgp39. The purified r-RgpA44 or r-Kgp39 protein can then be used to generate antibodies using standard techniques. The animals used for antibody generation can be rabbits, goats, chickens, sheep, horses, cows etc. When a high antibody titre against the r-RgpA44 or r-Kgp39 protein is detected by immunoassay the animals are bled or eggs or milk are collected and the serum prepared and/or antibody purified using standard techniques or monoclonal antibodies produced by fusing spleen cells with myeloma cells using standard techniques. The antibody (immunoglobulin fraction) may be separated from the culture or ascites fluid, serum, milk or egg by salting out, gel filtration, ion exchange and/or affinity chromatography, and the like, with salting out being preferred. In the salting out method the antiserum or the milk is saturated with ammonium sulphate to produce a precipitate, followed by dialyzing the precipitate against physiological saline to obtain the purified immunoglobulin fraction with the specific anti-r-RgpA44 or anti-r-Kgp39. The preferred antibody is obtained from the equine antiserum and the bovine antiserum and milk. In this invention the antibody contained in the antiserum and milk obtained by immunising the animal with the r-RgpA44 or r-Kgp39 protein or peptide is blended into the oral composition. In this case the antiserum and milk as well as the antibody separated and purified from the antiserum and milk may be used. Each of these materials may be used alone or in combination of two or more. Antibodies against the r-RgpA44 or r-Kgp39 can be used in oral compositions such as toothpaste and mouthwash. The anti-r-RgpA44 or anti-rKgp39 antibodies can also be used for the early detection of *P. gingivalis* in subgingival plaque samples by a chairside Enzyme Linked Immunosorbent Assay (ELISA).

For oral compositions it is preferred that the amount of the above antibodies administered is 0.0001-50 g/kg/day and that the content of the above antibodies is 0.0002-10% by weight preferably 0.002-5% by weight of the composition. The oral composition of this invention which contains the above-mentioned serum or milk antibody maybe prepared and used in various forms applicable to the mouth such as dentifrice including toothpastes, toothpowders and liquid dentifrices, mouthwashes, troches, periodontal pocket irrigating devices, chewing gums, dental pastes, gingival massage creams, gargle tablets, dairy products and other foodstuffs. The oral composition according to this invention may further include additional well-known ingredients depending on the type and form of a particular oral composition.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 4.5 to about 9 and typically from about 5.5 to 8. The pH is preferably in the range of from about 6 to about 8.0, preferably The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

Other desirable forms of this invention, the oral composition may be substantially solid or pasty in character, such as toothpowder, a dental tablet or a dentifrice, that is a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimapesium phosphate, calcium carbonate, hydrated alumina, calcined alumina, aluminum silicate, zirconium silicate, silica, bentonite, and mixtures thereof. Other suitable polishing material include the particulate thermosetting resins such as melamine-, phenolic-, and urea-formaldehydes, and crosslinked polyepoxides and polyesters. Preferred polishing materials include crystalline silica having particle size of up to about 5 microns, a mean particle size of up to about 1. 1 n-Acrons, and a surface area of up to about 50,000 $cm^2$/gm, silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal aluminosilicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyidnylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labeled packages. Thus, a jar of mouthrinse will have a label describing it, in substance, as a mouthrinse or mouthwash and having directions for its use; and a toothpaste, cream or gel will usually be in a collapsible tube, typically aluminum, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, nonionic or ampholytic in nature which does not denature the antibody of the invention, and it is preferred to employ as the surface-active agent a detersive material which imparts to the composition detersive and foaming properties while not denaturing the antibody. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble nonionic surfactants; suitable for use with antibodies are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Surface active agent is typically present in amount of about 0.1-5% by weight. It is noteworthy, that the surface active agent may assist in the dissolving of the antibody of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavor and sweetening agents may each or together comprise from about 0.1% to 5% more of the preparation.

In the preferred practice of this invention an oral composition according to this invention such as mouthwash or dentifrice containing the composition of the present invention is preferably applied regularly to the gums and teeth, such as every day or every second or third day or preferably from 1 to 3 times daily, at a pH of about 4.5 to about 9, generally about 5.5 to about 8, preferably about 6 to 8, for at least 2 weeks up to 8 weeks or more up to a lifetime.

The compositions of this invention can be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plasticizers or softeners, sugar or other sweeteners or such as glucose, sorbitol and the like.

The composition of this invention also includes targeted delivery vehicles such as periodontal pocket irrigation devices, collagen, elastin, or synthetic sponges, membranes or fibres placed in the periodontal pocket or used as a barrier membrane or applied directly to the tooth root.

The following examples are further illustrative of the nature of the present invention, but it is understood that the invention is not limited thereto. All amounts and proportions referred to herein and in the appended claims are by weight unless otherwise indicated.

EXAMPLE 1

Cloning and expression of the *P. gingivalis* proteinase and adhesin domains RgpA45, RgpA44, RgpA27 and RgpA15 in *E. coli* and testing of the recombinant proteins as a vaccine in the murine abscess model.

TABLE 1

Oligonucleotide primers used for the amplification of the nucleotide sequences encoding RgpA45, RgpA44, RgpA27 and RgpA15.

| Recombinant Protein | Primers | |
|---|---|---|
| RgpA45 | Forward 5'-GCGCAGATCTTACACACCGGTAGAGG-3' | (SEQ ID NO.:9) |
| | Reverse 5'-GCGCGTCGACTTAGCGAAGAAGTTCGGGG-3' | (SEQ ID NO.:10) |
| RgpA44 | Forward 5'-GCGCCATATGAGCGGTCAGGCCGAGATTGTTCTTG-3' | (SEQ ID NO.:11) |
| | Reverse 5'-GCGCCTCGAGGCGCTTGCCATTGGCCTTGATCTC-3' | (SEQ ID NO.:12) |
| RgpA27 | Forward 5'-GCGCGCTAGCGTATACATGGCCAACGAAGCCAAGG-3' | (SEQ ID NO.:13) |
| | Reverse 5'-GCGCAGATCTCTTGATAGCGAGTTTCTC-3' | (SEQ ID NO.:14) |
| RgpA15 | Forward 5'-GCGCGCTAGCGTATACATGGCAGACTTCACGGAAACGTTC-3' | (SEQ ID NO.:15) |
| | Reverse 5'-GCGCAGATCTTTTGGCGCCATCGGCTTCCG-3' | (SEQ ID NO.:16) |

Each of the proteinase and adhesin domains of the gene rgpA were amplified using the primers listed in Table 1, *P. gingivalis* W50 genomic DNA with Elongase® (Gibco BRI) DNA polymerase and a PC-960 thermal cycler (Corbett Research Technologies). Using the oligonucleotide primers a PCR was performed essentially as described in the Elongase instruction protocol using the following conditions: 25 cycles of denaturation (94° C., 30 sec), annealing (50° C., 45 sec), and extension (70° C., 1.5 min). The PCR product was purified using PCR Spinclean® (Progen) and ligated into plasmid vector pGEMT-easy (Promega) and transformed into competent *E. coli* JM109 (Promega) following the manufacturers protocols. All procedures were similar for the preparation of the four recombinants so the detailed process for the RgpA44 only will be described. Recombinant plasmid pGEMT-easy-RgpA44 DNA was digested with NdeI and XhoI to release the insert DNA. Insert DNA was isolated by agarose gel electrophoresis (0.8%) and purified using the Qiafilter gel extraction kit (Qiagen). Purified insert DNA was ligated into Qiafilter purified plasmid expression vector pET28a (Novagen) that had been previously digested with NdeI and XhoI, and the ligation products were transformed into the non-expression host, *E. coli* JM109. The recombinant pET28-RgpA44 plasmid was then transformed into the *E. coli* expression host, HMS174(DE3) and selected on LB containing 50 μg kanamycin. The r-RgpA44 expressed from pET28a contains a hexahistidine tag fused to the N-terminus of the expressed recombinant protein. r-RgpA44 expression was induced by addition of IPTG and purified by nickel-affinity chromatography. The integrity of the insert of pET28-RgpA44 was confirmed by DNA sequence analysis.

Expression of Recombinant E. coli

A single colony transformant was used to inoculate 10 mls of Luria-Bertani broth containing 50 μg/ml kanamycin at 37° C. until the optical density ($OD_{600}$) was 1.0. This inoculum was then used to inoculate 500 ml of Terrific broth (containing potassium phosphates and 50 μg/ml kanamycin). The $OD_{600}$ of this culture was allowed to reach 2.0 before inducing with 0.1 mM IPTG. After a 4.5 hour induction period at 37° C. the culture was harvested by centrifuging at 4000 rpm for 20 min at 4° C. and the pellet was stored at −70° C. for the extraction of inclusion bodies.

Isolation and Solubilisation of Inclusion Bodies

The bacterial pellet was thawed on ice and resuspended in binding buffer (5 mM imidazole, 500 nM NaCl, 20 mM Tris-HCl, pH 7.9), then sonicated and centrifuged at 20,000×g to collect the inclusion bodies. The pellet was resuspended in binding buffer and the process of sonication and centrifugation repeated twice more to release further protein. The pellet was then resuspended in binding buffer containing 6 M urea and incubated on ice for 2-3 hrs stirring to completely dissolve proteins. Any remaining insoluble material was removed by centrifuging at 39,000×g for 20 min. The supernatant was filtered through a 0.45 μm membrane before column purification.

Nickel-nitrilotriaectic Acid (Ni-NTA) Purification and Refolding of Solubilised Inclusions Ni-NTA metal affinity chromatography was used to purify the recombinant proteins via the $H_6$ tag. Briefly, proteins were batch bound to the equilibrated Ni-NTA resin (Qiagen) which was poured into a small column and unbound proteins were eluted under gravity. The column was then washed with 10 volumes of binding buffer followed by 5 column volumes of wash buffer (60 mM imidazole, 500 mM NaCl, 20 mM Tris-HCl, 6M urea, pH 7.9). The bound protein was then eluted in buffer containing 1M imidazole, 500 mM NaCl, 20 mM Tris-HCl, 6M urea, pH 7.9).

Renaturation of Recombinant Protein

Fractions eluted off the NI-NTA resin were pooled and refolded by the step-wise dialysis from 6 M to 3 M to 1.5 M to 0 M Urea contained in the following buffer 0.5 M Tris-HCl, 50 mM NaCl and 8% Glycerol.

Polyacrylamide Gel Electrophoresis and Western Blotting

SDS-PAGE was performed as described by Laemmli. Samples were mixed with an equal volume of 2× sample reducing buffer, boiled for 10 min at 95° C. and ran on Tris-glycine 12% gels (Novex). Molecular weight standards (SeeBlue™) were also purchased from Novex. Western blots were prepared by electroblotting proteins onto nitrocellulose for 1 hr at 100 volts. Membranes were blocked with 1% casein solution before incubating with primary antibody diluted to 1/1000, washed and incubated with an goat anti-rabbit-BRP conjugate (KPL) washed and developed with TMB membrane peroxidase substrate (KPL).

Antisera

Polyclonal antiserum was raised to the purified recombinant proteins by dosing BALB/c mice with 2×20 μg of recombinant protein in Freunds incomplete adjuvant (Sigma) three weeks apart. Mice were bled one week after the second dose and the antiserum generated was used to screen Western blots of whole cell P. gingivalis W50 run under denaturing, reducing conditions.

The purity of the recombinant proteins was confirmed using MALDI-TOF mass spectrometry and N-terminal sequence analysis.

Murine Lesion Model

Groups of 10 female BALB/c mice (6-8 weeks old) were immunized (20 μg) subcutaneously with each recombinant protein, r-RgpA45, r-RgpA44, r-RgpA27 and r-RgpA15 as well as formalin-killed P. gingivalis cells and E. coli; all emulsified in Incomplete Freunds Adjuvant. The immunizations were given at the base of the tail and occurred four weeks and one week prior to challenge with P. gingivalis. Two days prior to challenge mice were bled from the retrobulbar plexus. BALB/c mice were challenged with $7.5 \times 10^9$ viable cells of P. gingivalis 33277 subcutaneously in the abdomen. Following challenge, mice were examined daily for the number and size of lesions over a period of seven days. Lesions developed on the abdomen of the mice and the maximum lesion size in $MM^2$ is presented in FIG. 1. Significant reductions in lesion size were obtained only with vaccination using formalin-killed whole P. gingivalis cells and the recombinant adhesin r-RgpA44. The other recombinant proteins from the rgpA gene did not significantly reduce lesion size.

This example demonstrates the superiority of r-RgpA44 over the other recombinant proteins from the rgpA gene in protection against P. gingivalis challenge.

EXAMPLE 2

In the previous example it was demonstrated that the recombinant 44 kDa adhesin protected against challenge with P. gingivalis in the mouse lesion model. However the full length 44 kDa adhesin when expressed in E. coli was found as inclusion bodies that were only soluble in denaturing solvents. A series of fragments from the 44 kDa adhesin were generated in order to improve the solublility of the protein and enhance the correct folding of the recombinant protein. The oligonucleotide primers used to construct fragments of the 44 kDa adhesin recombinant protein are shown in Table 2.

TABLE 2

Oligonucleotide primers used for construction of the r-protein vectors

| Recombinant Protein | Direction | Primers | |
|---|---|---|---|
| Fragment 1 | F | 5'-GGGAATTCCATGGGTCAGGCCGAGATTGTT-3' | (SEQ ID NO.:17) |
| Fragment 1 | R | 5'-TCCCTCGAGCTTAACTTCCACGCAATACTC-3' | (SEQ ID NO.:18) |
| Fragment 2 | F | 5'-GGGAATTCCATGGGTCAGGCCGAGATTGTT-3' | (SEQ ID NO.:19) |

TABLE 2-continued

Oligonucleotide primers used for construction of the r-protein vectors

| Recombinant Protein | Direction | Primers | |
|---|---|---|---|
| Fragment 2 | R | 5'-GGTCAATTGGACTCGAGATATACACAACCATTGCT-3' | (SEQ ID NO.:20) |
| Fragment 3 | F | 5'-GAGGAATTCAGATCCTTCTTGTTCCCCTAC-3' | (SEQ ID NO.:21) |
| Fragment 3 | R | 5'-TCCCTCGAGCTTAACTTCCACGCAATACTC-3' | (SEQ ID NO.:22) |
| Fragment 4 | F | 5'-GAGGAATTCAGATCCTTCTTGTTCCCCTAC-3' | (SEQ ID NO.:23) |
| Fragment 4 | R | 5'-GGTCAATTGGACTCGAGATATACACAACCATTGCT-3' | (SEQ ID NO.:24) |
| Fragment 5 | F | 5'-GAGGAATTCAGATCCTTCTTGTTCCCCTAC-3' | (SEQ ID NO.:25) |
| Fragment 5 | R | 5'-AGGAATTCTCGAGCTTGCCGTTGGCCTTGAT-3' | (SEQ ID NO.:26) |
| Fragment 6 | F | 5'-GGGAATTCCATGGCGAAGGTATGTAAAGACGTT-3' | (SEQ ID NO.:27) |
| Fragment 6 | R | 5'-GGTCAATTGGACTCGAGATATACACAACCATTGCT-3' | (SEQ ID NO.:28) |
| Fragment 7 | F | 5'-GGGAATTCCATGGCGAAGGTATGTAAAGACGTT-3' | (SEQ ID NO.:29) |
| Fragment 7 | R | 5'-AGGAATTCTCGAGCTTGCCGTTGGCCTTGAT-3' | (SEQ ID NO.:30) |

Using similar methods as described in Example 1, fragments of the 44 kDa adhesin were cloned into pET24b plasmids (Novagen) and expressed in *E. coli* strain BL21(DE3) (Novagen). Expression levels and the amount of soluble r-44 kDa protein produced were assessed for the different fragments. This was done following IPTG induction, where by a 1.5 ml cell culture of the recombinant *E. coli* cell culture was pelleted by centrifugation and resuspended in 150 ul of binding buffer. Cells were then sonicated for 10 sec using a microprobe at a setting of 5 (Virosonic Digital 475 ultrasonic cell disruptor, The Virtis Company, NY). Following centrifugation for 3 minutes (10,000 rpm) the supernatant was collected, which represented the soluble fraction. The pellet was then washed and the resuspended in binding buffer, which represented the insoluble fraction. Analysis of the various fractions was carried out using Western blot analysis and SDS-PAGE. The results of these experiments are shown in Table 3. The stability of the r-44 kDa protein or fragments thereof may also be further enhanced by the site directed mutagenisis of all or selected cysteine residues to serine or alanine residues.

The 44 kDa adhesin contains six Cys residues that form disulphides when oxidized which may result in incorrect folding and possibly lead to the formation of insoluble protein. The stability of the r-44 kDa protein or fragments of the r-44 kDa protein may therefore be further enhanced by the site directed mutagenisis of all or selected cysteine residues to serine or alanine residues.

TABLE 3

Expression levels and solubility of r-44 kD proteins

| 44 Kd construct | Residues | Size (amino acids) | Expression levels | Solubility |
|---|---|---|---|---|
| Full length | 1-419 | 419 | +++++ | – |
| Fragment 1 | 2-184 | 183 | +++++ | + |
| Fragment 2 | 2-290 | 289 | +++++ | ++ |
| Fragment 3 | 65-184 | 120 | +++++ | +++++ |

TABLE 3-continued

Expression levels and solubility of r-44 kD proteins

| 44 Kd construct | Residues | Size (amino acids) | Expression levels | Solubility |
|---|---|---|---|---|
| Fragment 4 | 65-290 | 226 | +++++ | +++++ |
| Fragment 5 | 65-418 | 352 | +++++ | – |
| Fragment 6 | 192-290 | 99 | +++++ | +++++ |
| Fragment 7 | 192-418 | 227 | +++++ | – |

The amino acid numbering is derived from SEQ ID NO 3.

FIG. 2 shows the results of the full length recombinant 44 kD protein, 2 fragments of the 44 kD protein (Fragment 4; residues 65-290 and fragment 6; residues 192-290) and a control recombinant protein R2 in the mouse abscess model as described in Example 1. Mice were given 2 doses of 20 ug of r-protein 3 weeks apart as in Example 1. Both the full length and the fragment forms of the 44 kD protein showed statistically significant protection (p<0.05) compared to the control recombinant protein (R2). Formalin killed whole *P. gingivalis* (FK-33277) gave complete protection from challenge.

EXAMPLE 3

In addition to using fragments of the 44 kDa adhesin, chimeric proteins may be constructed using one or more fragments of the 44 kDa adhesin with other proteins or protein fragments from other *P. gingivalis* proteins. Sequence ID 2 and 4 give one such example of a chimeric recombinant protein derived from a fragment of the 44 kDa adhesin (Fragment 6 residues 192-290) linked to another *P. gingivalis* protein fragment derived from PG33 (Genbank accession number AF175715) a 95 residue C terminal fragment (residues 286-380). In total this chimeric protein has a total of 194 residues.

This chimeric recombinant fusion protein of fragments from the 44 kDa and PG33 proteins was produced by amplifying the PG33 C-terminal fragment by PCR as described in Example 1 using the following primers.

```
                                              (SEQ ID NO.:31)
Forward:  5'GGCCCATGGTCGACAATAGTGCAAAGATTGAT 3'

(SEQ ID NO.:32)
Reverse:  5'CTATCCGGCCGCTTCCGCTGCAGTCATTACTACAA 3'
```

This PCR product was subcloned into the SalI and NotI sites of pET24b to generate pET24b::PG33C. The 44 kDa fragment 6 PCR product (see example 2 for primers) was then subcloned into the EcoRI and SalI of the pET24b::PG33C plasmid to generate a fusion construct of 44 kDa/PG33 i.e. pET24b::PG44f6-PG33C. When this plasmid was transformed into *E. coli* strain BL21(DE3) and expression studies performed as outlined in Examples 1 and 2, high levels of the chimeric 44 kDa/PG33 recombinant protein were obtained which was soluble when tested as in Example 2.

EXAMPLE 4

Mouse antisera raised to the recombinant 44 kDa or recombinant fragments of the 44 kDa protein react with paraformaldehyde fixed whole *P. gingivalis* cells indicating that immuno-reactive epitopes are conserved in the recombinant proteins.

Mouse antisera were obtained by immunising BALB/c mice with the recombinant full length 44 kDa protein or with a recombinant fragment of the 44 kDa protein as described in Examples 1 and 2. *P. gingivalis* (strain W50) was anaerobically grown to log phase in brain heart infusion broth (Oxoid) supplemented with 5 ug/ml hemin and 1ug/ml vitamin K and 0.5 mg/ml Cysteine. Cells were sedimented by centrifugation for 15 min at 10,000 rpm at 4° C. and resuspended in phosphate-buffered saline (PBS) containing 1% (wt/vol) paraformaldehyde. Bacteria were placed at 4° C. overnight, then washed and resuspended in PBS to an optical density of 0.25 at OD600 ($1 \times 10^9$ cells/ml). Killed bacteria were then mixed in 10 μl aliquots with pooled mouse polyclonal sera at a dilution of 1:100 in 0.22 μm filtered PBS+10% FBS+0.01% Azide (PBS/FA) for 15 min at room temperature. The cells were washed with PBS/FA and were subsequently incubated 15 min with 1 μl of FITC-labelled anti-mouse Immunoglobulin (Silenus) at a dilution of 1:100 in PBS/FA. The cells were then washed and resuspended in 1 ml of PBS/FA.

The fluorescence intensity of stained *P. gingivalis* cells was quantified using a FACS Calibur-activated fluorescence cell sorter (Becton Dickinson) using the 488 nm wavelength band generated from a 15 mW argon ion laser. Filtered PBS/FA was used as the sheath fluid. FITC emission signals were collected for each analysis which consisted of 20,000 gated events that were collected on the basis of size and granularity using CELLQuest software (Becton Dickinson).

The results are shown in FIG. 3. The % marked on each panel indicates the percentage of *P. gingivalis* cells staining positively i.e., with a fluorescence intensity above the background levels seen with no antisera or with sera from normal mice. All of the recombinant proteins produced antisera that reacted with the majority of *P. gingivalis* cells although antisera to Fragment 4 showed a reduced reactivity compared to the other r-44 kDa antisera.

EXAMPLE 5

Cloning and expression of the *P. gingivalis* Kgp39 (Kgp39) and Kgp39 fragment (Kgp39frag) adhesin domains in *E. coli* and testing of the recombinant proteins by ELISA

TABLE 4

Oligonucleotide primers used for the amplification of the nucleotide sequences encoding Kgp39

| Recombinant Protein | Primers | | |
|---|---|---|---|
| Kgp39 | Forward | 5'-GCAGCAGTCGACGCCAACGAAGCCAAGGTTG-3' | (SEQ ID NO.:33) |
|  | Reverse | 5'-GCAGCACTCGAGGCGCTTGCCATTGGCC-3' | (SEQ ID NO.:34) |
| Kgp39frag | Forward | 5'-GCAGCAGTCGACTTCTTGTTGGATGCCGATCAC-3' | (SEQ ID NO.:35) |
|  | Reverse | 5'-GCAGCACTCGAGGAATGATTCGGAAAGTGTTG-3' | (SEQ ID NO.:36) |

Kgp39 and Kgp39 fragment adhesin domains were amplified using the primers listed in Table 4. The primers consist of a 6 nucleotide buffer followed by a restriction enzyme site (SalI or XhoI) and sequence specific for Kgp39. PCR was performed using Taq DNA Polymerase (Promega) under the following conditions: 25 cycles of denaturation (94° C., 45 sec), annealing (52° C., 30 sec), and extension (72° C., 60 sec). The PCR product was ligated into plasmid vector pGEMT-easy (Promega) and transformed into competent *E. coli* JM109 (Promega) as previously described. All procedures were identical for the preparation of both Kgp39 and Kgp39 fragment recombinants and are essentially as described above for recombinant Rgp44 fragments. Recombinant plasmid pGEMT-easy-Kgp39 DNA was digested with SalI and XhoI and the purified insert DNA was ligated into purified plasmid expression vector pET28b (Novagen) that had been previously digested with SalI and XhoI. Ligation products were transformed into the non-expression host, *E. coli* JM109 and then transformed into the *E. coli* expression host, HMS174(DE3) as previously described. r-Kgp39 expression was induced by addition of IPTG and purified by nickel-affinity chromatography. The integrity of the insert of pET28b-Kgp39 was confirmed by DNA sequence analysis.

Expression of Recombinant *E. coli*

Recombinant Kgp39 and Kgp39 fragment proteins were expressed by induction with IPTG using similar methodology as that described for rRgp44 fragments. Briefly, single colony transformants were used to inoculate 5 ml LB containing 50 μg/ml kanamycin at 37° C. on an orbital shaker overnight. This culture was then used to inoculate 100 ml of fresh medium and grown to mid-log growth phase ($OD_{600}$=0.6-1.0) before inducing with 0.5 mM IPTG for 6 hours. Cells were then harvested by centrifugation at 6500×g and stored at −20° C. overnight for the extraction of inclusion bodies.

Isolation and Solubilisation of Inclusion Bodies

The bacterial pellet was thawed on ice and resuspended in 10 mls of buffer B (20 mM $Na_2HPO_4$, 0.5M NaCl, 8M urea). The redissolved cell pellet was sonicated on ice for 3×30 second bursts at 30 second intervals using a Branson Sonifier® 250 Cell disruptor (Branson Ultrasonics Corporation, Danbury, Conn.) with the microtip on setting 3. Insoluble cellular debris was removed by centrifugation at 39000×g for 30 minutes at 4° C. and the supernatant collected. The insoluble cellular fraction was resuspended in 10 mls of Buffer B. Sodium azide (0.001% v/v) was added to all samples prior to storage at 4° C. Samples were then analysed by SDS-PAGE.

Nickel-nitrilotriaectic Acid (Ni-NTA) Purification and Refolding of Solubilised Inclusions Proteins were purified using Pharmacia Biotech HiTrap affinity columns (1 ml) (Amersham Pharmacia Biotech) connected to a Pharmacia Fast Protein Liquid Chromatography (FPLC) instrument. The column was coated with 5 column volumes of 0.1M $NiSO_4$ then equilibrated with 10 column volumes of Start Buffer (20 mM $Na_2HPO_4$, 0.5M NaCl, 20 mM imidazole, 8M urea) at a flow rate of 1 ml/min. Samples were loaded onto the column at a flow rate of 0.5 ml/min, then washed with 10 volumes of Start Buffer at a rate of 1 ml/min. Protein was eluted over a linear gradient of 10 volumes of Elution Buffer (20 mM $Na_2HPO_4$, 0.5M NaCl, 200 mM imidazole, 8M urea) at a flow rate Of 1 ml/min. Elution fractions were collected and samples of each fraction were analysed on SDS-PAGE gels as previously described.

Renaturation of Recombinant Protein

Removal of 8M urea from the recombinant protein samples was achieved using Spectrum-Por® Float-A-Lyzer (Alltech, Australia). The molarity of urea in the samples was taken from 8M initially to 0M over a period of 4 days. rKgp39 proteins were refolded by step-wise dialysis from 8 M to 7 M to 6 M to 5 M to 4 M to 3 M to 2 M to 1 M to 0.5 M to 0 M Urea contained in the following buffer: 20 mM $Na_2HPO_4$, 0.5M NaCl Enzyme-linked Immunosorbent Assay (ELISA)

ELISAs were performed to investigate the binding of RgpA-Kgp specific antisera to rKgp39 and rKgp39 fragment and the binding of rKgp39 and rKgp38 fragment to periodontal matrices and host proteins.

Wells of flat-bottomed polyvinyl microtitre plates (Microtitre, Dynatech Laboratories, VA, USA) were coated with 5 µg/ml of either rKgp39 or rKgp39 fragment in 0.1M PBS [0.01M $Na_2HPO_4$, 0.15M NaCl, 1.5 mM $KH_2PO_4$, 3.0 mM KCl, pH 7.4] overnight at room temperature (RT). The coating solution was removed and wells were blocked with 1% (w/v) BSA in 0.1M PBST (PBS containing 0.1% (v/v) Tween 20), for 1 hour at RT and plates washed 4× with 0.1M PBST. Serial dilutions of rabbit antisera directed against the P. gingivalis W50 RgpA-Kgp proteinase-adhesin complex (Bhogal et al., 1997) was added to each well and incubated overnight at RT and then washed with 6×PBST. Bound antibody was detected by incubation with horseradish peroxidase-conjugated goat immunoglobulin directed against mouse immunoglobulin (1:4000 dilution) (Sigma, NSW, Australia) in 0.5% (w/v) BSA in 0.1M PBS for 1.5 hr at RT. The plates were then washed (6×PBST) and substrate [0.9 mM ABTS (2,2'-azinobis(3-ethylbenz-thiazoline-6-) sulfonic acid], and 0.005% (v/v) $H_2O_2$, in ABTS buffer (0.1M $Na_2HPO_4$, 0.08 M citric acid monohydrate) (100 µl/well) was added. The optical density at 415 nm ($O.D_{415}$) was measured by using a Bio-Rad microplate reader (model 450, BioRad, NSW, Australia).

The results are shown in FIG. 4.

Binding of rKgp39 and rKgp39 Fragment to Periodontal Matrices and Host Proteins

ELISAs were also performed to investigate the binding characteristics of rKgp39 and rKgp39 fragment proteins to the host matrix proteins fibrinogen and collagen type V and to haemoglobin. Microtitre plates were coated with 10 g/ml of either fibrinogen, collagen type V or haemoglobin in 0.1M PBS overnight at RT. The coating solution was removed and remaining uncoated plastic was blocked with 2% (w/v) Skim milk in 0.1M PBST for 1 hr at RT. The blocking solution was removed and 5 µg/ml of either rKgp39 or rKgp39 fragment protein in 0.1M PBS was added to wells and incubated for 2 hr at RT. Wells were washed 4× with 0.1M PBST, then serial dilutions of rabbit anti-RgpA-Kgp complex anti-sera in 1% (w/v) Skim milk in 0.1M PBST was added to each well and incubated overnight at RT. Bound antibody was detected, after washing 6×PBST, by incubation with horseradish peroxidase conjugated goat immunoglobulin directed against rabbit immunoglobulin (1:4000 dilution) (Sigma, NSW, Australia) in 1%(w/v) Skim milk in 0.1M PBST for 1 hr at RT. The plates were developed as described above.

The results are shown in FIGS. 5 and 6.

EXAMPLE 6

This example illustrates that nucleotide sequences encoding RgpA44 or Kgp39 or portions thereof, can be inserted into, and expressed by various vectors including phage vectors and plasmids. Successful expression of the protein and peptides requires that either the insert comprising the gene or gene fragment, or the vector itself, contain the necessary elements for transcription and translation which is compatible with, and recognized by the particular host system used for expression. DNA encoding the RgpA44 or Kgp39 or fragments thereof (e.g. Example 2), or related peptides or oligopeptides or chimeric peptides can be synthesized or isolated and sequenced using the methods and sequences as illustrated herein. A variety of host systems may be utilized to express the RgpA44 or Kgp39 or fragments thereof, related peptides or oligopeptides or chimeras, which include, but are not limited to bacteria transformed with a bacteriophage vector, plasmid vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc.).

Using methods known in the art of molecular biology, including methods described above, various promoters and enhancers can be incorporated into the vector or the DNA sequence encoding RgpA44 or Kgp39 amino acid sequences, i.e., related peptides or oligopeptide or chimeras, to increase the expression of the RgpA44 or Kgp39 amino acid sequences, provided that the increased expression of the amino acid sequences is compatible with (for example, non-toxic to) the particular host cell system used. Thus and importantly, the DNA sequence can consist of the genes segment encoding the RgpA44 or Kgp39 or fragments thereof, or any other segment or combined segments of the domain which encode functional and specific epitopes of the protein. Further, the DNA can be fused to DNA encoding other antigens, such as other bacterial outer membrane proteins, or other bacterial, fungal, parasitic, or viral antigens to create a genetically fused (sharing a common peptide backbone) multivalent antigen for use as an improved vaccine composition.

The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription have been observed in a host cell system comprising E. coli include the lac promoter, trp promoter, recA promoter, ribosomal RNA promoter, the PR and $P_L$ promoters, lacUV5, ompF, bla, lpp, and the like, may be used to provide transcription of the inserted DNA sequence encoding amino acid sequences.

Additionally, if protein, related peptides or oligopeptides or chimeras may be lethal or detrimental to the host cells, the host cell strain/line and expression vectors may be chosen such that the action of the promoter is inhibited until specifically induced. For example, in certain operons the addition of specific inducers is necessary for efficient transcription of the inserted DNA (e.g., the lac operon is induced by the addition of lactose or isopropylthio-beta-D-galactoside). A variety of operons such as the trp operon, are under different control mechanisms. The trp operon is induced when tryptophan is absent in the growth media. The $P_L$ promoter can be induced by an increase in temperature of host cells containing a temperature sensitive lambda repressor. In this way, greater than 95% of the promoter-directed transcription may be inhibited in uninduced cells. Thus, expression of recombinant RgpA44 protein, related peptides, or oligopeptides or chimeras may be controlled by culturing transformed or transfected cells under conditions such that the promoter controlling the expression from the inserted DNA encoding RgpA44 amino acid sequences is not induced, and when the cells reach a suitable density in the growth medium, the promoter can be induced for expression from the inserted DNA.

Other control elements for efficient gene transcription or message translation include enchancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the inserted DNA sequences encoding RgpA44 or Kgp39 amino acid sequences to increase transcriptional efficiency. As illustrated previously in this example, other specific regulatory sequences have been identified which may effect the expression from the gene segment encoding RgpA44 or Kgp39 and related peptides or chimeras. These or other regulatory sites, such as transcription or translation initiation signals, can be used to regulate the expression of the gene encoding RgpA44 or Kgp39, or gene fragments thereof. Such regulatory elements may be inserted into DNA sequences encoding RgpA44 or Kgp39 amino acid sequences or nearby vector DNA sequences using recombinant DNA methods described herein for insertion of DNA sequences.

Accordingly, P. gingivalis nucleotide sequences containing regions encoding for RgpA44 or Kgp39, related peptides, or oligopeptides or chimeras can be ligated into an expression vector at a specific site in relation to the vector's promoter, control, and regulatory elements so that when the recombinant vector is introduced into the host cell the P. gingivalis-specific DNA sequences can be expressed in the host cell. For example, the RgpA44 or Kgp39 specific DNA sequence containing its own regulatory elements can be ligated into an expression vector in a relation or orientation to the vector promoter and control elements which will allow for expression of the RgpA44 or Kgp39 or derivatives. The recombinant vector is then introduced into the appropriate host cells, and the host cells are selected, and screened for those cells containing the recombinant vector. Selection and screening may be accomplished by methods known in the art including detecting the expression of a marker gene (e.g., drug resistance marker) present in the plasmid, immunoscreening for production of RgpA44 or Kgp39 specific epitopes using antisera generated to RgpA44 or Kgp39 specific epitopes, and probing the DNA of the hosts cells for RgpA44 or Kgp39 specific nucleotide sequence using one or more oligonucleotide sequences and methods described herein.

Genetic engineering techniques may also be used to characterize, modify and/or adapt the encoded RgpA44 or Kgp39 recombinant or protein. For example, site-directed mutagenesis of RgpA44 or Kgp39 or fragments thereof to modify one or all Cys residues to Ser or Ala residues may be desirable to increase the stability and solubility of the recombinant protein to allow for easier purification and folding. Further, genetic engineering techniques can be used to generate DNA sequences encoding a portion of the amino acid sequence of RgpA44 or Kgp39 in particular, soluble, hydrophilic sequences corresponding to protective epitopes. Restriction enzyme selection may be done so as not to destroy the immunopotency of the resultant peptide or oligopeptide or chimera. Antigenic sites of a protein may vary in size but can consist of from about 7 to about 14 amino acids. Thus, RgpA44 or Kgp39 will contain many discrete antigenic sites; therefore, many partial gene sequences could encode antigenic epitopes of RgpA44 or Kgp39. These sequences can be constructed and used in an expression system to generate highly antigenic chimeric peptides or oligopeptides or proteins. Combinations of two or more peptides may result in increased immunogenicity. When using combinations of antigens these antigens may be related (i.e. from the same gene sequence or from a closely related gene from the same organism). The antigens may be generated from a related organism (i.e. another oral bacterium present in subgingival plaque), or from a more distantly-related organism. In particular the host organism for the vector containing the RgpA44 or Kgp39 related genes and constructs can be a commensal inhabitant of the oral cavity; for example an inhabitant of subgingival plaque, supragingival plaque or a bacterium associated with the oral mucosa. Examples of commensal intra-oral bacteria would be Streptococcus species and Actinomyces species, e.g. Streptococcus salivarius, Streptococcus sanguis, Actinomyces naeslundii. These organisms can be isolated from the periodontitis patient and then genetically engineered to express the RgpA44 or Kgp39 or components, peptides or chimeras. The DNA encoding the RgpA44 or Kgp39, peptides or chimeras could be linked with DNA encoding leader sequences of extracellular proteins of these commensal intra-oral bacteria. The DNA encoding the RgpA44 or Kgp39 or derivatives could also be linked with, or inserted into, the DNA encoding extracellular proteins to produce secreted fusion proteins. Examples of extracellular proteins that could be used to produce fusion proteins with the RgpA44 or Kgp39, components, peptides or chimeras could be the glucosyltranferases (GTF) or fructosyltransferases (FTF). The recombinant organism would be then re-introduced into the patients oral cavity and once colonised the oral mucosa or teeth would express the RgpA44 or Kgp39, component, peptide, chimera or fusion to stimulate the mucosal associated lymphoid tissue to produce neutralising antibodies.

The DNA fragment encoding an antigen may be fused to other DNA sequences to allow for improved expression and/or purification procedures (i.e. DNA sequences cloned into the vector pTrxFus, are expressed as fusions to the *E. coli* protein thioredoxin). This linkage imparts the characteristics of thioredoxin to the fusion protein which offers soluble expression of normally insoluble or difficult to express proteins. After purification, the native protein is released by removal of the entire thioredoxin by digestion with enterokinase. Furthermore, the antigen may be used as a hapten by fusion to other sequences which may increase immunogenicity, if the expressed protein or peptide is not immunogenic.

Another plasmid expression system involves the pUC-derived pTrcHis expression vector from Invitrogen. This vector allows high-level expression of DNA sequences by the presence of the Trc promoter (containing the –35 region of the Trp promoter together with the –10 region of the lac promoter) and an rrnB anti-terminator element. The pTrcHis vectors also contain a copy of the lacI$^q$ gene which encodes the lac repressor protein. Therefore, expression of the recombinant protein/peptide is induced by addition of 1 mM IPTG (derepression) to *E. coli* grown to mid-log phase. The DNA fragment is inserted into the multiple cloning site which is positioned downstream and in frame with a sequence that encodes an N-terminal fusion peptide. The N-terminal fusion peptide encodes (from 5' to 3'); an ATG translation initiation codon, a series of 6 histidine residues that function as a metal-binding domain in the translated protein, a transcript stabilising sequence from gene 10 of phage T7, and an enterokinase cleavage recognition sequence. Cell culture lysates of cells harbouring the recombinant plasmid are purified by high-affinity binding to Probond™ resin (Invitrogen). Probond™ is a nickel-charged sepharose resin that is used to purify recombinant proteins containing a poly-histidine binding domain. Bound proteins are eluted from the Probond™ resin with either low pH buffer or by competition with imidazole or histidine. The polym-histidine leader peptide may be subsequently removed by digestion of the recombinant expressed protein with Enterokinase. Enterokinase recognizes the endopeptidase recognition sequence that is engineered between the poly-his affinity tag and the multiple cloning site in the vector to allow for cleavage of the poly-His tail away from the protein of interest. The purified, recombinant protein may then be used in the generation of antibodies, vaccines and the formulation of diagnostic assays as discussed.

EXAMPLE 7

Methods for using RgpA44 or Kgp39 specific nucleotide sequences in molecular diagnostic assays for the detection of *P. gingivalis*. The nucleic acid sequences of the present invention can be used in molecular diagnostic assays for detecting *P. gingivalis* genetic material. In particular, RgpA44 or Kgp39 sequence-specific oligonucleotides can be synthesized for use as primers and/or probes in amplifying, and detecting amplified, nucleic acids from *P. gingivalis*. Recent advances in molecular biology have provided several means for enzymatically amplifying nucleic acid sequences. Currently the most commonly used method, PCR™ (polymerase chain reaction Cetus Corporation) involved the use of Taq Polymerase, known sequences as primers, and heating cycles which separate the replicating deoxyribonucleic acid (DNA) strands and exponentially amplify a gene of interest. Other amplification methods currently under development include LCR™ (ligase chain reaction, BioTechnica International) which utilizes DNA ligase, and a probe consisting of two halves of a DNA segment that is complementary to the sequence of the DNA to be amplified; enzyme QB replicase (Gene-Trak Systems) and a ribonucleic acid (RNA) sequence template attached to a probe complementary to the DNA to be copied which is used to make a DNA template for exponential production of complementary RNA; and NASBA® (nucleic acid sequence-based amplification, Cangene Corporation) which can be performed on RNA or DNA as the nucleic acid sequence to be amplified.

Nucleic acid probes that are capable of hybridization with specific gene sequences have been used successfully to detect specific pathogens in biological specimens at levels of sensitivity approaching $10^3$-$10^4$ organisms per specimen [1990, Gene Probes for Bacteila, eds. Macario and deMacario, Academic Press]. Coupled with a method that allows for amplification of specific target DNA sequences, species-specific nucleic acid probes can greatly increase the level of sensitivity in detecting organisms in a clinical specimen. Use of these probes may allow direct detection without relying on prior culture and/or conventional biochemical identification techniques. This embodiment of the present invention is directed to primers which amplify species-specific sequences of the gene encoding RgpA44 or Kgp39 of *P. gingivalis*, and to probes which specifically hybridize with these amplified DNA fragments. By using the nucleic acid sequences of the present invention and according to the methods of the present invention, as few as one *P. gingivalis* organism may be detected in the presence of 10 ug/ml extraneous DNA.

This embodiment is directed to species-specific oligonucleotides which can be used to amplify sequences of *P. gingivalis* DNA, if present, from DNA extracted from clinical specimens including subgingival plaque, sputum, blood, abscess and other fluids to subsequently determine if amplification has occurred. In one embodiment of the present invention, a pair of *P. gingivalis*-specific DNA oligonucleotide primers are used to hybridize to *P. gingivalis* genomic DNA that may be present in DNA extracted from a clinical specimen, and to amplify the specific segment of genomic DNA between the two flanking primers using enzymatic synthesis and temperature cycling. Each pair of primers are designed to hybridize only to the *P. gingivalis* nucleotide sequences of the present invention to which they have been synthesized to complement; one to each strand of the double-stranded DNA. Thus, the reaction is specific even in the presence of microgram quantities of heterologous DNA. For the purposes of this description, the primer derived from the sequence of the positive (gene) strand of DNA will be referred to as the "positive primer", and the primer derived from the sequence of the negative (complementary) strand will be referred to as the "negative primer". Amplification of DNA may be accomplished by any one of the methods commercially available. For example, the polymerase chain reaction may be used to amplify the DNA. Once the primers have hybridized to opposite strands of the target DNA, the temperature is raised to permit replication of the specific segment of DNA across the region between the two primers by a thermostable DNA polymerase. Then the reaction is thermocycled so that at each cycle the amount of DNA representing the sequences between the two primers is doubled, and specific amplification of the *P. gingivalis* DNA sequences, if present, results. Further identification of the amplified DNA fragment, as being derived from *P. gingivalis* DNA, may be accomplished by liquid hybridization. This test utilizes one or more labeled oligonucleotides as probes to specifically hybridize to the amplified segment of *P. gingivalis* DNA. Detection of the presence of sequence-specific amplified DNA may be accomplished using any one of several methods known in the art such as a gel retardation assay with autoradiography. Thus, the nucleotide sequences of the present invention provide basis for the synthesis of oligonucleotides which have commercial applications in diagnostic kits for the detection of *P. gingivalis*. In a related embodiment, the oligonucleotides used as primers may be labeled directly, or synthesized to incorporate label. Depending on the label used, the amplification products can then be detected, after binding onto an affinity matrix, using isotopic or colorimetric detection.

DNA may be extracted from clinical specimens which may contain *P. gingivalis* using methods known in the art. For example, cells contained in the specimen may be washed in TE buffer and pelleted by centrifugation. The cells then may be resuspended in 100 ul of amplification reaction buffer containing detergents and proteinase K. Using the polymerase chain reaction, the resultant sample may be composed of the cells in 10 mM Tris pH 8.3, 50 mM KCl, 1.5 mM $MgCl_2$, 0.01% gelatin, 0.45% NP40™, 0.045% Tween 20™, and 60 ug/ml proteinase K. The sample is incubated in a 55° C. water bath for 1 hour. Following the incubation, the sample is incubated at 95° C. for 10 minutes to heat-inactivate the proteinase K. The sample may then be amplified in accordance with the protocol for the polymerase chain reaction as set forth below.

The *P. gingivalis* DNA may be amplified using any one of several protocols for amplifying nucleic acids by the polymerase chain reaction. In one mode of this embodiment, the gene encoding the RgpA44 or Kgp39 may be amplified from clinical isolates of *P. gingivalis* using the following conditions. DNA to be amplified (1 mg of genomic DNA) is distributed to 0.5 ml microfuge tubes and the volume adjusted to 50 ul by adding a reaction mixture comprising 0.2 mM dNTPs (dATP, dCTP dGTP, dTTP), 0.25 ug of each positive and negative oligonucleotide primer, 1 unit of TaqI polymerase, TaqI 10× buffer (5 ul), 1 mM $MgCl_2$ (final concentration), and sterile distilled water to achieve the total volume. The TaqI polymerase is added to the reaction mixture just before use and is gently mixed, not vortexed. A layer of mineral oil, approximately 2 drops, is added to each tube and then the tubes are placed in the thermal cycler. Thirty to thirty-five cycles are general sufficient for bacterial DNA amplification. One cycle consists of 1 minute at 95° C., 1 minute at 37° C., and 1 minute at 72° C. The first cycle includes a 1½ minute incubation at 95° C. to assure complete denaturation.

Oligonucleotides useful as primers or probes which specifically hybridize to the gene encoding the RgpA44 or Kgp39 of *P. gingivalis* and used in DNA amplification and/or detection can be biochemically synthesized, using methods known in the art, from the nucleotide sequences in the Sequence ID listings herein. For detection purposes, the oligonucleotides of the present invention may be end-labeled with a radioisotope. Probe sequences, internal to the two primers used for amplification of the gene sequence, may be end-labeled using T4 polynucleotide kinase and gamma $^{32}P$ ATP. Twenty pMols of probe DNA in kinase buffer (50 mM Tris, pH 7.6 10 mM $MgCl_2$, 5 mM dithiothreitol, 0.1 mM spermidine-HCl, 0.1 mM EDTA, pH 8.0) is mixed with 120 uCi of gamma $^{32}P$ ATP and incubated at 37° C. for 1 hour. Labeled probe is separated from unincorporated label on an 8% acrylamide gel run for 1 hour at 200 volts in Tris Borate EDTA (TBE) buffer at room temperature. Labeled probe is first located by exposing the acrylamide gel to x-ray film for three minutes. The resulting autoradiogram is then positioned under the gel, and the band containing the labeled probe was excised from the gel. The gel slice is pulverized in one milliliter of sterile distilled water, and the probe is eluted by shaker incubation overnight at 37° C. The eluted probe is separated from the gel fragments by centrifugation using a chromatography prep column. Radioactivity of the probe is determined, by counting one microliter of the labeled probe on a glass fibre filter, by liquid scintillation. Such probe sequences may be chosen from any of the sequences disclosed herein provided the probe sequence is internal to the two primers used for amplification of the desired nucleotide sequence disclosed in the present invention.

Alternative methods known in the art may be used to improve the detection of amplified target sequences in accordance with the compositions and methods of the present invention. The sensitivity of detection of the amplified DNA sequences can be improved by subjecting the sequences to liquid hybridization. Alternative methods of detection known in the art, in addition to gel electrophoresis and gel electrophoresis with Southern hybridization and autoradiography, that may be used with the compositions and methods of the present invention include: restriction enzyme digestion with gel electrophoresis; slot-blot hybridization with a labeled oligonucleotide probe; amplification with a radiolabeled oligonucleotide probe; amplification with a radiolabeled primer with gel electrophoresis, Southern hybridization and autoradiography; amplification with a radiolabeled primer with dot blot and autoradiography; amplification with oligonucleotides containing affinity tags (ex. biotin, or one primer incorporating biotin and the other primer with a sequence specific for a DNA binding protein) followed by detection in an affinity-based assay (ex. ELISA); and amplification with oligonucleotides containing fluorophores followed by fluorescence detection.

One embodiment of non-isotopic detection involves incorporating biotin into the oligonucleotide primers of the present invention. The 5'-amino group of the primers may be biotinylated with sulfo-NHS-biotin, or biotin may be incorporated directly into the primer by synthesizing the primer in the presence of biotin-labeled dNTPs. The non-isotopic labeled primers are then used in amplifying DNA from a clinical specimen. The detection for the presence or absence of amplified target sequences may be accomplished by capturing the amplified target sequences using an affinity matrix having avidin bound thereto, followed by incubation with an avidin conjugate containing an enzyme which can be used to visualize the complex with subsequent substrate development. Alternatively, the amplified target sequences may be immobilized by hybridization to the corresponding probes of the target sequence wherein the probes have been affixed onto a matrix. Detection may be accomplished using an avidin conjugate containing an enzyme which can be used to visualize the complex with subsequent substrate development.

EXAMPLE 8

Methods for Using RgpA44 or Kgp39, Peptides or Chimeric Peptides in Diagnostic Immunoassays.

The RgpA44 or Kgp39 protein, related peptides, oligopeptides or chimeras can be purified for use as immunogens in vaccine formulations; and as antigens for diagnostic assays or for generating *P. gingivalis*-specific antisera of therapeutic and/or diagnostic value. The RgpA44 or Kgp39 from *P. gingivalis* or oligopeptides or peptides or chimeras thereof, or recombinant protein, recombinant peptides, or recombinant oligopeptides produced from an expression vector system, can be purified with methods known in the art including detergent extraction, chromatography (e.g., ion exchange, affinity, immunoaffinity, or ultrafiltration and sizing columns), differential centrifugation, differential solubility, or other standard techniques for the purification of proteins.

As used throughout the specification, RgpA44 or Kgp39 oligopeptides are defined herein as a series of peptides corresponding to a portion of the amino acid sequence of the RgpA44 or Kgp39 respectively as disclosed in the enclosed sequences that are synthesized as one or chemically-linked. Such peptides or oligopeptides can be synthesized using one of the several methods of peptide synthesis known in the art including standard solid phase peptide synthesis using tert-butyloxycarbonyl amino acids [Mitchell et al., 1978, J. Org. Chem. 43:2845-2852], using 9-fluorenylmethyloxycarbonyl amino acids on a polyamide support [Dryland et al., 1986, J. Chem. So. Perkin Trans. 1,125-137]; by pepscan synthesis [Geysen et al., 1987, J Immunol Methods 03:259; 1984; and Proc. Natl. Acad. Sci. USA 81:3998]; by standard liquid phase peptide synthesis; or by recombinant expression vector systems. Modification of the peptides or oligopeptides, such as by deletion and substitution of amino acids (and including extensions and additions to amino acids) and in other ways, may be made so as to not substantially detract from the immunological properties of the peptide or oligopeptide. In particular, the amino acid sequences of the RgpA44 or Kgp39, or peptide or oligopeptide or chimera thereof, may be altered by replacing one or more amino acids with functionally equivalent amino acids resulting in an alteration which is silent in terms of an observed difference in the physicochemical behaviour of the protein, peptide, or oligopeptide or chimera. Functionally equivalent amino acids are known in the art as amino acids which are related and/or have similar polarity or charge. Thus, an amino acid sequence which is substantially that of the amino acid sequences depicted in the Sequence Listing herein, refers to an amino acid sequence that contains substitutions with functionally equivalent amino acids without changing the primary biological function of protein, peptide, or oligopeptide or chimera.

Purified RgpA44 or Kgp39 protein, peptides, oligopeptides and chimeras may be used as antigens in immunoassays for the detection of *P. gingivalis*-specific antisera present in the body fluid of an individual suspected of having an infection caused by *P. gingivalis*. The detection of RgpA44 or related peptides as an antigen in immunoassays, includes any immunoassay known in the art including, but not limited to, radioimmunoassay, enzyme-linked immunosorbent assay (ELISA), "sandwich" assay, precipitin reaction, agglutination assay, fluorescent immunoassay, and chen-liluniinescence-based immunoassay.

EXAMPLE 9

Methods and Compounds for Vaccine Formulations Related to RgpA44 or Kgp39 and Related Peptides and Chimeras.

This embodiment of the present invention is to provide recombinant RgpA44 or Kgp39 protein and/or peptides or oligopeptides or chimeras thereof, to be used in as immunogens in a prophylactic and/or therapeutic vaccine for active immunization to protect against or treat infections caused by *P. gingivalis*. For vaccine purposes, an antigen of *P. gingivalis* comprising a bacterial protein should be immunogenic, and induce functional antibodies directed to one or more surface-exposed epitopes on intact bacteria, wherein the epitope(s) are conserved amongst strains of *P. gingivalis*.

For vaccine development, RgpA44 or Kgp39 specific amino acid sequences may be purified from a host containing a recombinant vector which expresses RgpA44 or Kgp39 or related peptides or chimeras. Such hosts include, but are not limited to, bacterial transformants, yeast transformants, filamentous fungal transformants, and cultured cells that have been either infected or transfected with a vector which encodes RgpA44 or Kgp39 amino acid sequences. The recombinant protein, peptide, or oligopeptide or chimera immunogen is included as the relevant immunogenic material in the vaccine formulation, and in therapeutically effective amounts, to induce an immune response. Many methods are known for the introduction of a vaccine formulation into the human or animal to be vaccinated. These include, but are not limited to, intradermal, intramuscular, intraperitoneal, intravenous, subcutaneous, ocular, intranasal, and oral administration. The vaccine may further comprise a physiological carrier such as a solution, a polymer or liposomes; and an adjuvant, or a combination thereof.

Various adjuvants are used in conjunction with vaccine formulations. The adjuvants aid by modulating the immune response and in attaining a more durable and higher level of immunity using smaller amounts of vaccine antigen or fewer doses than if the vaccine antigen were administered alone. Examples of adjuvants include incomplete Freund's adjuvant (IFA), Adjuvant 65 (containing peanut oil, mannide monooleate and aluminum monostrearate), oil emulsions, Ribi adjuvant, the pluronic polyols, polyamines, Avridine, Quil A, saponin, MPL, QS-21, and mineral gels such as aluminium salts. Other examples include oil in water emulsions such as SAF-1, SAF-0, MF59, Seppic ISA720, and other particulate adjuvants such as ISCOMs™ and ISCOM matrix™. An extensive but not exhaustive list of other examples of adjuvants are listed in Cox and Coulter 1992 [Wong, W K (ed.) Animals parasite control utilising technonolgy. Bocca Raton; CRC press, 1992; 49-112]. In addition to the adjuvant the vaccine may include conventional pharmaceutically acceptable carriers, excipients, fillers, buffers or diluents as appropriate. One or more doses of the vaccine containing adjuvant may be administered prophylactically to prevent periodontitis or therapeutically to treat already present periodontitis.

In another preferred composition the preparation is combined with a mucosal adjuvant and administered via the oral route. Examples of mucosal adjuvants are cholera toxin and heat labile *E. coli* toxin, the non-toxic B subunits of these toxins, genetic mutants of these toxins which have a reduced toxicity. Other methods which may be utilised to deliver RgpA44 orally include incorporation of the protein into particles of biodegradable polymers (such as acrylates or polyesters) by microencapsulation to aid uptake of the microspheres from the gastrointestinal tract and to protect degradation of the proteins. Liposomes, ISCOMs™, hydrogels are examples of other potential methods which may be further enhanced by the incorporation of targeting molecules such as LTB, CTB or lectins for delivery of the RgpA44 protein or peptide to the mucosal immune system. In addition to the vaccine and the mucosal adjuvant or delivery system the vaccine may include conventional pharmaceutically acceptable carriers, excipients, fillers, coatings, dispersion media, antibacterial and antifungal agents, buffers or diluents as appropriate.

Another embodiment of this mode of the invention involves the production of recombinant RgpA44 or Kgp39 specific amino acid sequences as a hapten, i.e. a molecule which cannot by itself elicit an immune response. In such case, the hapten may be covalently bound to a carrier or other immunogenic molecule which will confer immunogenicity to the coupled hapten when exposed to the immune system. Thus, such a RgpA44 or Kgp39 specific hapten linked to a carrier molecule may be the immunogen in a vaccine formulation.

Another mode of this embodiment provides for either a live recombinant viral vaccine, recombinant bacterial vaccine, recombinant attenuated bacterial vaccine, or an inactivated recombinant viral vaccine which is used to protect against infections caused by *P. gingivalis*. Vaccinia virus is the best known example, in the art, of an infectious virus that is engineered to express vaccine antigens derived from other organisms. The recombinant live vaccinia virus, which is attenuated or otherwise treated so that it does not cause disease by itself, is used to immunize the host. Subsequent replication of the recombinant virus within the host provides a continual stimulation of the immune system with the vaccine antigens such as recombinant RgpA44 or Kgp39 protein, related peptides or chimeras, thereby providing long lasting immunity.

Other live vaccine vectors include: adenovirus, cytomegalovirus, and preferably the poxyiruses such as vaccinia [Paoletti and Panicali, U.S. Pat. No. 4,603,112] and attenuated *Salmonella* strains [Stocker et al., U.S. Pat. Nos. 5,210,035, 4,837,151 and 4,735,801; and Curtiss et al., 1988, Vaccine 6:155-160]. Live vaccines are particularly advantageous because they continually stimulate the immune system which can confer substantially long-lasting immunity. When the immune response is protective against subsequent *P. gingivalis* infection, the live vaccine itself may be used in a preventive vaccine against *P. gingivalis*. In particular, the live vaccine can be based on a bacterium that is a commensal inhabitant of the oral cavity. This bacterium can be transformed with a vector carrying a recombinant RgpA44 or Kgp39, peptides, oligopeptides or chimeric peptides and then used to colonise the oral cavity, in particular the oral mucosa. Once colonised the oral mucosa, the expression of the recombinant protein, peptide or chimera will stimulate the mucosal associated lymphoid tissue to produce neutralising antibodies. To further illustrate this mode of the embodiment, using molecular biological techniques such as those illustrated in Example 8, the genes encoding the RgpA44 or Kgp39 or gene fragments encoding one or more peptides or chimeras may be inserted into the vaccinia virus genomic DNA at a site which allows for expression of epitopes but does not negatively affect the growth or replication of the vaccinia virus vector. The resultant recombinant virus can be used as the immunogen in a vaccine formulation. The same methods can be used to construct an inactivated recombinant viral vaccine formulation except that the recombinant virus is inactivated, such as by chemical means known in the art, prior to use as an immunogen and without substantially affecting the immunagenicity of the expressed immunogen. A mixture of inactivated viruses which express different epitopes may be used in the formulation of a multivalent inactivated vaccine. In either case, the inactivated recombinant vaccine or mixture of inactivated viruses may be formulated with a suitable adjuvant in order to enhance the immunological response to the vaccine antigens.

In another variation of this embodiment, genetic material is used directly as the vaccine formulation. Nucleic acid (DNA or RNA) containing sequences encoding the RgpA44 or Kgp39 protein, related peptides or oligopeptides or chimeras, operatively linked to one or more regulatory elements can be introduced directly to vaccinate the individual ("direct gene transfer") against pathogenic strains of *P. gingivalis*. Direct gene transfer into a vaccinated individual, resulting in expression of the genetic material by the vaccinated individual's cells such as vascular endothelial cells as well as the tissue of the major organs, has been demonstrated by techniques in the art such as by injecting intravenously an expression plasmid: cationic liposome complex [Zhu et al., 1993, Science 261: 209-211]. Other effective methods for delivering vector DNA into a target cell are known in the art. In one example, purified recombinant plasmid DNA containing viral genes has been used to inoculate (whether parentally, mucosally, or via genegun immunization) vaccines to induce a protective immune response [Fynan et cd. 1993, Proc Natl. Acad Sci USA 90:11478-11482]. In another example, cells removed from an individual can be transfected or electroporated by standard procedures known in the art, resulting in the introduction of the recombinant vector DNA into the target cell. Cells containing the recombinant vector DNA may then be selected for using methods known in the art such as via a selection marker expressed in the vector, and the selected cells may then be re-introduced into the individual to express the RgpA44 or Kgp39 protein, related peptides or oligopeptides or chimeras.

One preferred method of vaccination with genetic material comprises the step of administering to the individual the nucleic acid molecule that comprises a nucleic acid sequence that encodes the RgpA44 or Kgp39 protein, related peptides, or oligopeptides or chimeras, wherein the nucleic acid molecule is operatively linked to one or more regulatory sequences necessary for expression. The nucleic acid molecule can be administered directly, or first introduced into a viral vector and administered via the vector. The nucleic acid molecule can be administered in a pharmaceutically acceptable carrier or diluent and may contain compounds that can enhance the effectiveness of the vaccine. These additional compounds include, but are not limited to, adjuvants that enhance the immune response, and compounds that are directed to modulate the immune response, e.g. cytokines, collectively referred to as "immune modulators"; or other compounds which increase the uptake of nucleic acid by the cells, referred to as "nucleic acid uptake enhancers". The immunization with the nucleic acid molecule can be through any parental route (intravenous, intraperitoneal, intradermal, subcutaneous, or intramuscular), or via contact with mucosal surfaces of the nasopharynx, trachea, or gastrointestinal tract.

As an alternative to active immunization, immunization may be passive, i.e. immunization comprising administration of purified immunoglobulin containing antibody against RgpA44 or Kgp39 epitopes.

EXAMPLE 10

The following is a proposed example of a toothpaste formulation containing anti-RgpA44 or anti-Kgp39 antibodies.

| Ingredient | % w/w |
|---|---|
| Dicalcium phosphate dihydrate | 50.0 |
| Glycerol | 20.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Chlorhexidine gluconate | 0.01 |
| Dextranase | 0.01 |
| Goat serum containing anti-RgpA44 or anti-Kgp39 | 0.2 |
| Water | balance |

EXAMPLE 11

The following is another proposed example of a toothpaste formulation.

| Ingredient | % w/w |
| --- | --- |
| Dicalcium phosphate dihydrate | 50.0 |
| Sorbitol | 10.0 |
| Glycerol | 10.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine serum containing anti-RgpA(788-1004) | 0.2 |
| Water | balance |

EXAMPLE 12

The following is another proposed example of a toothpaste formulation.

| Ingredient | % w/w |
| --- | --- |
| Dicalcium phosphate dihydrate | 50.0 |
| Sorbitol | 10.0 |
| Glycerol | 10.0 |
| Sodium carboxymethyl cellulose | 1.0 |
| Lauroyl diethanolamide | 1.0 |
| Sucrose monolaurate | 2.0 |
| Flavour | 1.0 |
| Sodium sacchrain | 0.1 |
| Sodium monofluorophosphate | 0.3 |
| Chlorhexidine gluconate | 0.01 |
| Dextranase | 0.01 |
| Bovine milk Ig containing anti-Rgp44 | 0.1 |
| Water | balance |

EXAMPLE 13

The following is another proposed example of a toothpaste formulation.

| Ingredient | % w/w |
| --- | --- |
| Sorbitol | 22.0 |
| Irish moss | 1.0 |
| Sodium Hydroxide (50%) | 1.0 |
| Gantrez | 19.0 |
| Water (deionised) | 2.69 |
| Sodium Monofluorophosphate | 0.76 |
| Sodium saccharine | 0.3 |
| Pyrophosphate | 2.0 |
| Hydrated alumina | 48.0 |
| Flavour oil | 0.95 |
| anti-Rgp44 monoclonal | 0.3 |
| sodium lauryl sulphate | 2.00 |

EXAMPLE 14

The following is a proposed example of a liquid toothpaste formulation.

| Ingredient | % w/w |
| --- | --- |
| Sodium polyacrylate | 50.0 |
| Sorbitol | 10.0 |
| Glycerol | 20.0 |
| Flavour | 1.0 |
| Sodium saccharin | 0.1 |
| Sodium monofluorophosphate | 0.3 |
| Chlorhexidine gluconate | 0.01 |
| Ethanol | 3.0 |
| Equine Ig containing anti-RpgA (788-1004) | 0.2 |
| Linolic acid | 0.05 |
| Water | balance |

EXAMPLE 15

The following is a proposed example of a mouthwash formulation.

| Ingredient | % w/w |
| --- | --- |
| Ethanol | 20.0 |
| Flavour | 1.0 |
| Sodium saccharin | 0.1 |
| Sodium monofluorophosphate | 0.3 |
| Chlorhexidine gluconate | 0.01 |
| Lauroyl, diethanolamide | 0.3 |
| Rabbit Ig containing anti-Rpg44 | 0.2 |
| Water | balance |

EXAMPLE 16

The following is a proposed example of a mouthwash formulation.

| Ingredient | % w/w |
| --- | --- |
| Gantrez S-97 | 2.5 |
| Glycerine | 10.0 |
| Flavour oil | 0.4 |
| Sodium monofluorophosphate | 0.05 |
| Chlorhexidine gluconate | 0.01 |
| Lauroyl diethanolamide | 0.2 |
| Mouse anti-Rpg44 monoclonal | 0.3 |
| Water | balance |

EXAMPLE 17

The following is a proposed example of a lozenge formulation.

| Ingredient | % w/w |
| --- | --- |
| Sugar | 75-80 |
| Corn syrup | 1-20 |

-continued

| Ingredient | % w/w |
| --- | --- |
| Flavour oil | 1.2 |
| NaF | 0.01-0.05 |
| Mouse anti-Rpg44 monoclonal | 0.3 |
| Mg stearate | 1.5 |
| Water | balance |

EXAMPLE 18

The following is a proposed example of a gingival massage cream formulation.

| Ingredient | % w/w |
| --- | --- |
| White petrolatum | 8.0 |
| Propylene glycol | 4.0 |
| Stearyl alcohol | 8.0 |
| Polyethylene Glycol 4000 | 25.0 |
| Polyethylene Glycol 400 | 37.0 |
| Sucrose monostearate | 0.5 |
| Chlorohexidine gluconate | 0.1 |
| Mouse anti-RpgA44 monoclonal | 0.3 |
| Water | balance |

EXAMPLE 19

The following is a proposed example of a chewing gum formulation.

| Ingredient | % w/w |
| --- | --- |
| Gum base | 30.0 |
| Calcium carbonate | 2.0 |
| Crystalline sorbitol | 53.0 |
| Glycerine | 0.5 |
| Flavour oil | 0.1 |
| Rabbit anti-RgpA (788-1004) monoclonal | 0.3 |
| Water | balance |

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An antigenic composition, the composition comprising at least one isolated and purified protein having a molecular weight of less than or equal to 44 kDa as estimated by SDS-PAGE under reducing conditions, wherein the isolated and purified protein consists of a sequence selected from the group consisting of SEQ. ID. NO. 3, residues 1-184 of SEQ. ID. NO. 3, residues 1-290 of SEQ. ID. NO. 3, residues 65-184 of SEQ. ID NO. 3, residues 65-290 of SEQ. ID. NO. 3, residues 192-290 of SEQ ID No:3, and residues 147-419 of SEQ. ID. NO. 3.

2. The antigenic composition as claimed in claim 1 in which the isolated and purified protein is soluble in non-denaturing solvents.

3. The antigenic composition as claimed in claim 1 in which the isolated and purified protein consists of a sequence selected from the group consisting of residues 65-184 of SEQ ID NO: 3, residues 65-290 of SEQ ID NO: 3 and residues 192-290 of SEQ ID NO: 3.

4. The antigenic composition as claimed in claim 1 in which the antigenic composition further comprises an adjuvant.

5. The antigenic composition as claimed in claim 2 in which the antigenic composition further comprises an adjuvant.

6. The antigenic composition as claimed in claim 3 in which the antigenic composition further comprises an adjuvant.

7. A method of reducing the severity of P. gingivalis infection in a subject, the method comprising administering to the subject the antigenic composition as claimed in claim 4, wherein the isolated and purified protein consists of a sequence selected from the group consisting of SEQ ID No. 3, residues 65-290 of SEQ ID No. 3, and residues 192-290 of SEQ No. 3.

8. A method of reducing the severity of P. gingivalis infection in a subject, the method comprising administering to the subject the antigenic composition as claimed in claim 5, wherein the isolated and purified protein consists of a sequence selected from the group consisting of SEQ ID No. 3, residues 65-290 of SEQ ID No. 3, and residues 192-290 of SEQ ID No.3.

9. An antigenic composition, the composition comprising a chimeric or fusion protein, wherein the chimeric or fusion protein comprises a first and a second polypeptide, wherein the first polypeptide consists of a sequence selected from the group consisting of SEQ. ID. NO. 3, residues 1-184 of SEQ. ID. NO. 3, residues 1-290 of SEQ. ID. NO. 3, residues 65-184 of SEQ. ID NO. 3, residues 65-290 of SEQ. ID. NO. 3, residues 192-290 of SEQ ID No:3, and residues 147-419 of SEQ. ID. NO. 3, and the second polypeptide comprises a *P. gingivalis* sequence.

10. The antigenic composition as claimed in claim 9 in which the chimeric or fusion protein is soluble in non-denaturing solvents.

11. The antigenic composition as claimed in claim 10 in which the first polypeptide of the chimeric or fusion protein consists of a sequence selected from the group consisting of residues 65-184 of SEQ ID NO: 3, residues 65-290 of SEQ ID NO: 3 and residues 192-290 of SEQ ID NO: 3.

12. The antigenic composition of claim 9, wherein the chimeric or fusion protein further comprises a sequence of another protein.

* * * * *